United States Patent [19]

Seoane et al.

[11] Patent Number: 5,510,380
[45] Date of Patent: Apr. 23, 1996

[54] NONPEPTIDE BRADYKININ ANTAGONISTS

[75] Inventors: Peter R. Seoane, Coatesville; Joseph M. Salvino, Schwenksville; Brent D. Douty, Coatesville; Mohamed M. A. Awad, Frazer; Roland E. Dolle, King of Prussia; David G. Sawutz, Mohnton; David M. Faunce, Collegeville; Wayne T. Houck, Spring City, all of Pa.

[73] Assignee: Sterling Winthrop, Inc., New York, N.Y.

[21] Appl. No.: 19,955

[22] Filed: Feb. 19, 1993

[51] Int. Cl.⁶ .......................... A61K 31/16; C07C 103/30
[52] U.S. Cl. .......................... 514/613; 514/620; 564/197; 564/198
[58] Field of Search .......................... 514/613, 620; 564/197, 198

[56] References Cited

U.S. PATENT DOCUMENTS

| | | | |
|---|---|---|---|
| 3,935,266 | 1/1976 | Hashimoto et al. | 564/197 |
| 4,242,329 | 12/1980 | Claeson et al. | 514/18 |
| 4,332,822 | 6/1982 | Ward | 424/324 |
| 4,602,041 | 7/1986 | Newsome et al. | 514/634 |
| 4,801,613 | 1/1989 | Stewart et al. | 514/14 |

OTHER PUBLICATIONS

CA 75:20936m "Guanidines", from Nowak, Kornel (Akad. Med., Wroclan, Pol.) Rocz. Chem., 44 (10) 1905–10 (Pol.) 1970.

*Primary Examiner*—Philip Tucker
*Assistant Examiner*—Catherine Kilby Scalzo
*Attorney, Agent, or Firm*—William J. Davis; Paul E. Dupont; Imre (Jim) Balogh

[57] ABSTRACT

Disclosed are nonpeptides having bradykinin antagonist activity of the formulae (I) and (II)

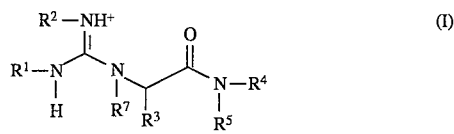

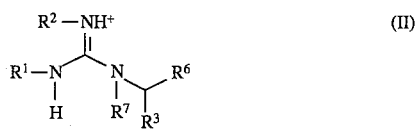

or a pharmaceutically acceptable salt thereof, pharmaceutical compositions containing the compound and methods of treating diseased or pathological conditions using the pharmaceutical compositions.

12 Claims, No Drawings

NONPEPTIDE BRADYKININ ANTAGONISTS

BACKGROUND OF THE INVENTION

1. Field of the Invention

This invention relates to novel nonpeptide compounds having bradykinin antagonist activity, their pharmaceutically acceptable salts, process for their preparation, pharmaceutical compositions containing the novel nonpeptides having bradykinin antagonist activity, and method of treating diseased conditions in a mammal including inflammation, pain, irregular blood pressure and irregular smooth muscle contractility. Specifically, the invention relates to novel, nonpeptide antagonist molecules with high affinity at the human bradykinin $B_2$ receptor.

2. Reported Developments

The nonapeptide bradykinin (Arg-Pro-Pro-Gly-Phe-Pro-Phe-Arg) Seg. ID NO. 1 is enzymatically released by kallikreins from precursor molecules (kininogens) in plasma and tissue (Proud and Kaplan, (1988) *Ann. Rev. Immunol.* 6:49) in response to trauma, tissue injury or activation of the kallikrein system by any means. The cellular effects of bradykinin are mediated through specific cell surface receptors (Plevin and Own, (1988) *Trends, Pharmacol. Sci.*, 9:387). Bradykinin receptors have been initially divided into two classes, $B_1$ and $B_2$, based on the activity of selective receptor antagonists for the $B_1$ receptor (Regoli and Barabe, (1980) *Pharmacol. Rev.* 32(1):1). Bradykinin activation of bradykinin receptors leads to intracellular signalling events resulting in the activation of the arachidonic acid cascade to produce prostaglandins and leukotrienes.

Bradykinin is released in the early stages following tissue injury and possesses several properties which implicate its role in the inflammatory events of rheumatoid arthritis. These include the ability to: (a) induce vasodilation; (b) enhance vascular permeability; (c) induce pain; and (d) induce synthesis and release of arachidonic acid metabolites. Bradykinin has been demonstrated to play a role in a variety of physiological functions including pain, inflammation, regulations of blood pressure and smooth muscle contractility (Rocha e Silva et al, (1949) *Am. J. Physiol.* 156:261; Regoli, (1983) *Adv. Exp. Med, Biol.* 156A:569). Examples and literature references include the following:

Bradykinin is one of the most potent pain producing substances (Collier et al, (1963) *Br. J. Pharmacol.* 21:151). The application of bradykinin to the free nerve endings of a blister base in humans has been shown to produce pain (Armstrong et al, (1957) *J. Physiol.* 135:350). The intraperitoneal or intraarterial administration of bradykinin has also been shown to produce pain in man. The production of pain in humans or the demonstration of hyperalgesia in experimental animals occurs primarily in association with an inflammatory component. Increased levels of circulating bradykinin have been demonstrated in acute (oral surgery) and chronic (rheumatoid arthritis) inflammatory states (Hargreaves et al., (1988) *Clinical Pharmacology & Therapeutics*, 44:163).

Bradykinin antagonists (substituted bradykinin peptide analogues) have been shown to be anti-inflammatory as well as antinociceptive. The inflammation and hyperalgesia produced by the intraplantar injection of carrageenan has been shown to be antagonized by NPC-567 (Costello and Hargreaves, (1989) *European J. Pharmacol.*, 171:259; Burch and DeHaas, (1990) *N. S. Arch. Pharmacol.*, 342:189). Steranka et al, (1988; *Proc. Natl. Acad. Sci.*, 85:3245) have demonstrated that NPC-567 and NPC-349 are antinociceptive in several different animal models of nociception/hyperalgesia. In humans, the pain produced by the application of bradykinin to a blister base was also antagonized by $B_2$ selective antagonists (Whalley et al, (1987) *Naunyn-Schmeid. Arch. Pharmacol.* 336:652).

Bradykinin is one of the primary mediators in the production of the inflammatory response. Bradykinin ilicits all of the cardinal signs of inflammation and has been identified in inflammatory exudates (Marceau et al, (1983) *Gen. Pharmacol.* 14:209). Synovial fluids from patients with rheumatoid arthritis, gout and psoriatic arthritis have been shown to contain elevated kinin levels (Jasani et al, (1969) *Ann. Rheum. Dis.* 28:497), whereas lower levels were reported from non-inflammatory joints (Eisen, V. (1970) *Br. J. Exp. Pathol.* 51:322). Intra-articular injection of bradykinin into dogs has been shown to cause an acute inflammatory response (Lerner et al, (1987) Arth. Rheum. 30:530). Bradykinin has been reported to stimulate the production of prostacyclin and $PGE_2$, known mediators in inflammation, from fibroblasts and endothelial cells (Bareis et al, (1983) *Proc. Natl. Acad. Sci.* 80:2514; Leikauf et al, (1985) *Am. J. Physiol.* 248:48). Recently bradykinin was shown to modulate the IL-1 induced release of $PGE_2$ from human synovial fibroblasts (Bathon et al, (1989) *J. Immunol.* 143:579). It has also been reported that human synovial fibroblasts from rheumatoid arthritis patients express bradykinin receptors and that following binding, bradykinin stimulates the production of $PGE_2$ (Uhl et al, (1992) *Immunopharm.* 23:131). In addition, bone resorption and matrix degradation have been demonstrated with bradykinin (Lerner et al, (1987) *Arth. Rheumat.* 30:530).

Bradykinin has been postulated to be a mediator of upper airway disease and asthma (Farmer, (1991) Bradykinin Antagonists: *Basic and Clinical Research*, R. M. Burch Edt., 213). Bradykinin is very potent at producing bronchoconstriction in asthmatics (Herxheimer and Stresemann, *J. Physiol.*, 158:38P). Bradykinin is also postulated to be involved in rhinoviral infections since it has been shown that subjects who become infected and symptomatic show increased kinin levels in nasal lavages (Naclerio et al, (1988) *J. Inf. Dis.* 157:133; Proud et al, (1990) *J. Inf. Dis.*, 161:120). Furthermore, it has been demonstrated that nasal provocation with bradykinin induces symptoms of rhinitis and a sore throat (Proud et al, (1988) *Am. Rev. Respir.. Dis.*, 137:613). A study of the intranasal bradykinin antagonist NPC-567, however, failed to demonstrate beneficial effects on the course of an experimentally induced rhinovirus infection (Bernstein et al, (1990) *Antiviral Res. Suppl.* 1:119). The reasons for the apparent inactivity of this compound are unknown and could reflect problems with drug delivery or metabolism.

Bradykinin, acting through specific cell surface receptors on endothelial cells, is one of the most potent agents that induces vasodilation and plasma extravasation (Regoli and Barabe, (1980) *Pharmacol. Rev.*, 32(1):1). These physiological effects may lead to exacerbation of pathophyisological states associated with shock, ischemia secondary to head trauma, and tumor metastasis.

There is significant evidence in the literature that activation of the kinin/kallikrein cascade is associated with endotoxin mediated shock (Aasen et al (1983) Arch. Surg., 118:343; Katori et al, (1989) *Br. J. Pharmcol.* 98"1381). The evidence for this includes 1) elevated levels of free bradykinin and enhanced plasma kallikrein activity in plasma treated with endotoxin; 2) endotoxin-induced dose-dependent decreases in blood pressure parallel the increase in free plasma kinin levels and the decrease in plasma HMW kininogen; and 3) attenuation of the hypotensive response and increased bradykinin levels by soybean trypsin inhibitor. Recent studies have demonstrated that the hypotensive responses and even the mortality associated with endotoxin-induced sepsis in the rat is dramatically reduced by bradykinin peptide antagonists (Weipert et al (1988) *Br. J. Pharmacol.* 94:282; Wilson et al (1989) *Circulatory Shock*, 27:93).

Ischemic brain damage occurring soon after head trauma is believed to be mediated largely by increases in intracranial pressure resulting from edema caused by plasma extravisation at or near the site of injury. Cerebral administration of bradykinin to rats (Kamiya, (1990) *Nippon Ika Daigaku Zasshi*, 57(2):180) or dogs (Unterberg and Baethmann, (1984) *J. Neurosurg.*, 61:87) induces cerebral edema. Enhancement of plasma kinin levels (5–10 fold over control) has been demonstrated during the reperfusion period following a 3-hour ischemic insult in rats (Kamiya, (1990) *Nippon Ika Daigaku Zasshi*, 57(2):180). This suggests that formation of kinins may be enhanced when cerebral blood flow becomes compromised by an increase in intra-cranial pressure.

Bradykinin has demonstrated mitogenic activity in some cell lines. Roberts and Gullick (1989) *J. Cell Sci.*, 94:527) have proposed a model in which the production of bradykinin by reactive inflammatory cells within tumors or the production of bradykinin during disruption of blood vessels may provide a paracrine stimulation of the growth of tumors expressing mutant ras oncogene with increased sensitivity to bradykinin. This stimulation may promote both tumor growth and speed. Recently significantly elevated levels of bradykinin in ascitic fluid from human cervical carcinoma and gastric carcinoma solid tumors has been observed providing further support for a role for bradykinin in metastatic disease syndromes.

There appears to be sufficient circumstantial evidence to suggest that bradykinin plays a role in irritable bowel syndrome. Kinin levels in patients with inflammatory bowel disease correlate well with the onset of vasomotor and gastrointestinal symptoms (1964; *Lancet* i 514–517; (1966) *Lancet* ii 986–991; (1971) *Br. Med. J.*, 3:565–566; (1974) *Annls. Int. Med.* 80:577–581). Inflamed intestinal tissue from patients with ulcerative colitis shown high kallikrein levels (Gut (1978) 14:133–138). Bradykinin has been shown to affect gut motility (Regoli and Barabe, (1980) *Pharmacol. Rev.* 32:1) and bradykinin receptors have been shown to mediate a chloride secretion form the intestinal serosa to the mucosa, but apparently not in the reverse direction. (*Nature* (1982) 299:256–259). Most cases of clinical diarrhea are due to ion and fluid secretion into the lumen, not altered gut motility. (Pathologic Physiology: Mechanisms of Disease, (1974) Sodeman and Sodeman, Eds.; 767–789. W. B. Saunders, Philadelphia).

Stewart and Vavrek (1985), *Peptides*, 6:161; U.S. Pat. No. 4,693,993, issued Sep. 15,1987) describes the first bradykinin $B_2$ peptide antagonists. The critical substitution involves the replacement of the L-proline residue in the number 7 position with an amino acid in the D-configuration; most specifically D-phenylalanine. These modified peptides have antagonist activity in a variety of assay systems (Stewart and Vavrek (1990) *J. Cardiovasc. Pharmacol.* 15 (Suppl. 6):S69), but also display agonist activity (Sawutz et al, (1992) *Eur. J. Pharmacol.*, 227:309). The compounds promote mast cell degranulation (Devillier et al, (1988) *Eur. J. Pharmacol*, 149:137) and are rapidly cleaved at several positions, including the 8–9 bond, which significantly decreases their receptor binding activity. Replacement of arginyl residues at positions 1 and 9 in addition to N-terminal and specific C-terminal extensions, results in increased enzyme resistance and antagonist potency (Stewart et al, International Patent Applications Nos. PCT/US88/02959 and PCT/US88/02960; issued Mar. 9, 1989).

In two recent patents by Henke et al (EP 0 413 277 A1; Feb. 20,1991) and by Nestor et al (EP 0 472 220 A1; Feb 26, 1992), key replacements of Pro$^7$ by 1,2,3,4-tetahydroisoquinoline-3-carboxylic acid (Tic) and Phe$^8$ by octahydroindole-2-carboxylic acid (Oic) resulted in novel bradykinin peptide antagonists. These, and other changes, resulted in compounds with significantly increased potency at the bradykinin receptor (approximately 2 orders of magnitude compared to [D-Phe$^7$]-bradykinin) and greater metabolic stability.

It is an object of this invention to provide bradykinin receptor antagonists of a nonpeptide nature having high potency at the human bradykinin $B_2$ receptor. These advantages are demonstrated in recognized assays in which compounds of this invention exhibit high potency. This invention encompasses methods for preparing the compounds of the invention, including pharmaceutically acceptable salts, and therapeutic uses for compounds of this invention. Furthermore, this invention provides compositions for treatment of an individual wherein the pharmaceutical compositions comprises an effective amount of a compound of the invention and a compatible pharmaceutically acceptable carrier.

SUMMARY OF THE INVENTION

Accordingly, the present invention provides a nonpeptide bradykinin antagonist of formulae (I) and (II):

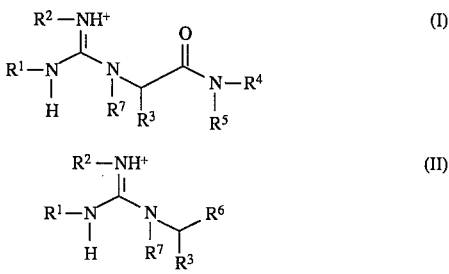

or a pharmaceutically acceptable salt thereof
wherein
$R^1$ and $R^2$ are independently H, substituted or unsubstituted alkyl, cycloalkyl or aryl in which one or two hydrogen atoms are optionally replaced by carboxy, lower-alkyl, hydroxy, halo, lower-alkoxyamino, or lower-alkylamino; preferably $R^1$ and $R^2$ are independently H,

lower-alkyl or phenyl;
$R^3$ is substituted or unsubstituted cycloalkyl, aryl, heteroaryl or aryloxy in which one, two or three hydrogen atoms on a carbon atom in the aromatic ring is optionally replaced by halo, carboxy, lower-alkyl or hydroxy; $R^3$ is preferably

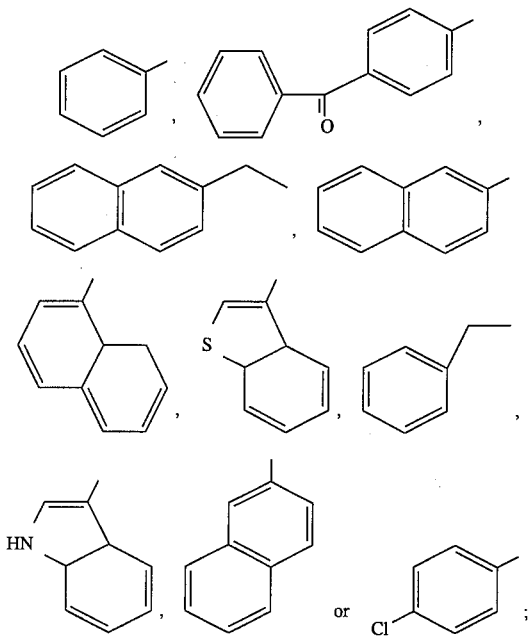

R⁴ is substituted or unsubstituted cycloalkyl, aryl, heteroaryl, aryloxy, heteroaryloxy, arylsulfonyl, in which one, two or three hydrogen atoms on a carbon atom is substituted by N, P, halo, carboxy, loweralkylamino or lower-alkyl hydroxy,

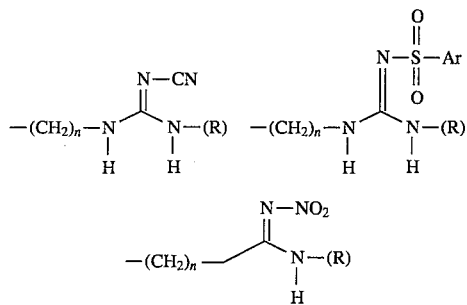

wherein
n is 1 to 4;
R is alkyl;
R⁴ is preferably

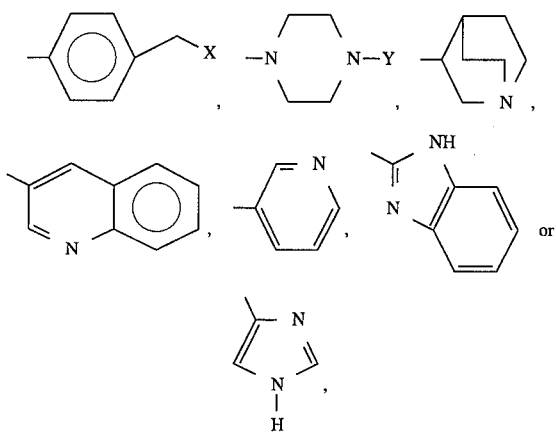

wherein X is $NY_2$, $PY_3$, $NR_2$, $NR_3$ lower-alkyl, cyclopentyl, cyclohexyl, amino-lower-alkyl or phenyl;
Y is alkyl, carbonyl or benzyl;
R⁵ is H or

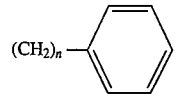

wherein n is 1 to 4;
R⁶ is

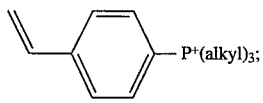

and
R⁷ is alkyl.

As used herein, the term halogen (or halo) means fluorine, chlorine, bromine or iodine.

As used herein, the term cycloalkyl means carbocyclic rings having from three to eight ring carbon atoms including cyclopropyl, cyclobutyl, cyclopentyl, cyclohexyl and cyclooctyl which may be substituted on any ring carbon atom thereof by one or more lower-alkyl groups, lower-alkoxy groups or halogens.

As used herein the terms lower-alkyl and lower-alkoxy mean monovalent aliphatic radicals, including branched chain radicals, of from one to ten carbon atoms. Thus, the lower-alkyl moiety of such groups include, for example, methyl, ethyl, propyl, isopropyl, n-butyl, sec-butyl, t-butyl, n-pentyl, 2-methyl-3-butyl, 1-methylbutyl, 2-methylbutyl, neopentyl, n-hexyl, 1-methylpentyl, 3-methylpentyl, 1-ethylbutyl, 2-ethylbutyl, 2-hexyl, 3-hexyl, 1,1,3,3-tetramethylpentyl, 1,1-dimethyloctyl and the like.

As used herein, the term aryl means an aromatic hydrocarbon radical having six to ten carbon atoms. The preferred aryl groups are phenyl, substituted phenyl and naphthyl substituted by from one to three, the same or different members of the group consisting of lower-alkyl, halogen, hydroxy-lower-alkyl, alkoxy-lower-alkyl and hydroxy.

As used herein, heteroaryl means mono or polycyclic aryl groups and include such groups as pyridyl, quinolyl, piperidyl, pyrrolyl, morpholinyl, thiomorpholinyl, furyl, furfuryl, tetrahydrofurfuryl, thienyl, tetrahydrothienyl, imidazolyl, benzimidozolyl and the like.

Pharmaceutically acceptable salts include alkali metal or alkaline ester metal salts, physiologically acceptable amines, and salts with inorganic or organic acids, such as HCl, HBr, $H_2SO_4$, $H_3PO_4$, maleic acid, fumaric acid, citric acid, tartaric acid, acetic acid, benzoic acid, succinic acid and cinnamic acid.

Compounds of the present invention may be synthesized according to the general synthetic schemes that follow utilizing commercially available starting materials. Alternatively, the starting materials may be made by methods known in the prior art.

Scheme 1

General Synthetic Scheme for Phosphonium, [[4-[[2-[[bis(cyclohexylamino)methylene]amino]-3-(2-naphthalenyl)-1-oxopropyl]amino]methyl]tributyl-, chloride, monohydrochloride and Analogs 5,510,380

7
-continued
Scheme 1

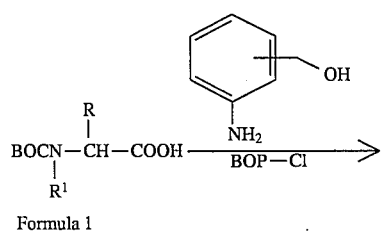

Formula 1

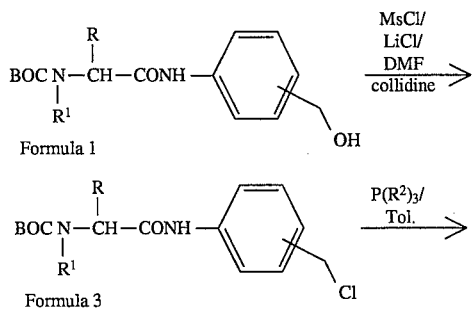

Formula 3

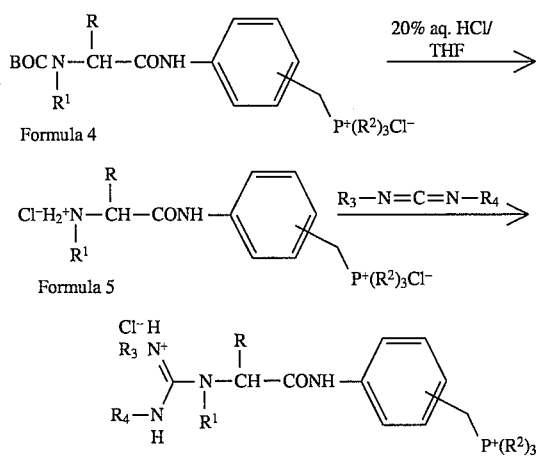

Formula 5 wherein R is H, CH$_2$Ph, CH$_2$CH$_2$Ph,

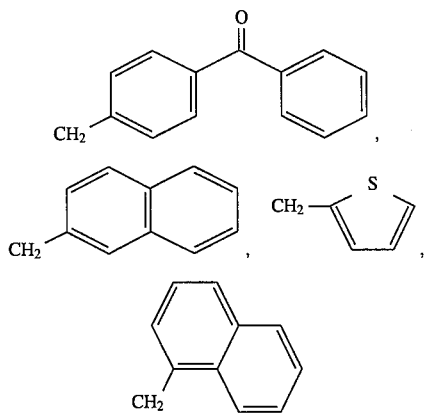

R$^1$ is butyl, CH$_3$
R$^2$ is butyl, pentyl
R$^3$ is cyclohexyl, isopropyl, propyl, pCH$_3$C$_6$H$_5$
R$^4$ is cylcohexyl, isopropyl, CH$_2$CH$_2$CH$_3$PhpCH$_3$C$_6$H$_5$ Scheme 2

General Synthetic Scheme for 2-Naphthalenepropanamide, N-1-

8
-continued
Scheme 2 azabicyclo[2.2.2]oct-3-yl-α-[[bis(cyclohexylamino)methylene]amino]-
dihydrochloride and Analogs
(Head Group Modifications)

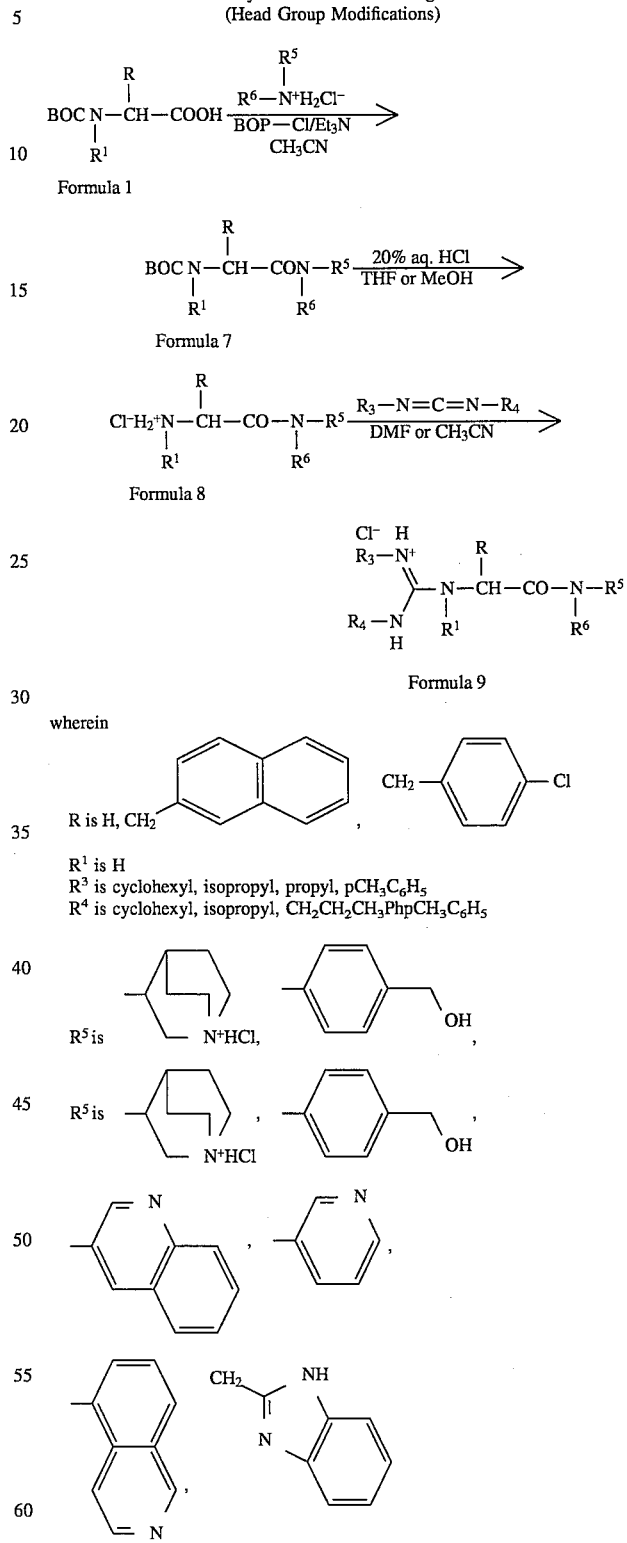

wherein

R is H, CH$_2$- (naphthyl), CH$_2$- (p-Cl-phenyl)

R$^1$ is H
R$^3$ is cyclohexyl, isopropyl, propyl, pCH$_3$C$_6$H$_5$
R$^4$ is cyclohexyl, isopropyl, CH$_2$CH$_2$CH$_3$PhpCH$_3$C$_6$H$_5$ R$^5$ is quinuclidinyl-N$^+$HCl, p-hydroxybenzyl, R$^5$ is quinuclidinyl-N$^+$HCl, p-hydroxybenzyl, isoquinolinyl, pyridyl, isoquinolinyl-CH$_2$, benzimidazolyl

Scheme 3

General Synthetic Scheme for the Replacement of the Amide Bond, Phosphonium, [[4-[3-[[bis(cyclohexylamino)methylene]amino]-4-(2-naphthalenyl)-1-cis-butenyl]phenyl]methyl]tributyl-, chloride, monohydrochloride and Phosphonium, [[4-[3-[[bis(cyclohexylamino)methylene]amino]-4-(2-naphthalenyl)-1-trans-butenyl]phenyl]methyl]tributyl-, chloride, monohydrochloride

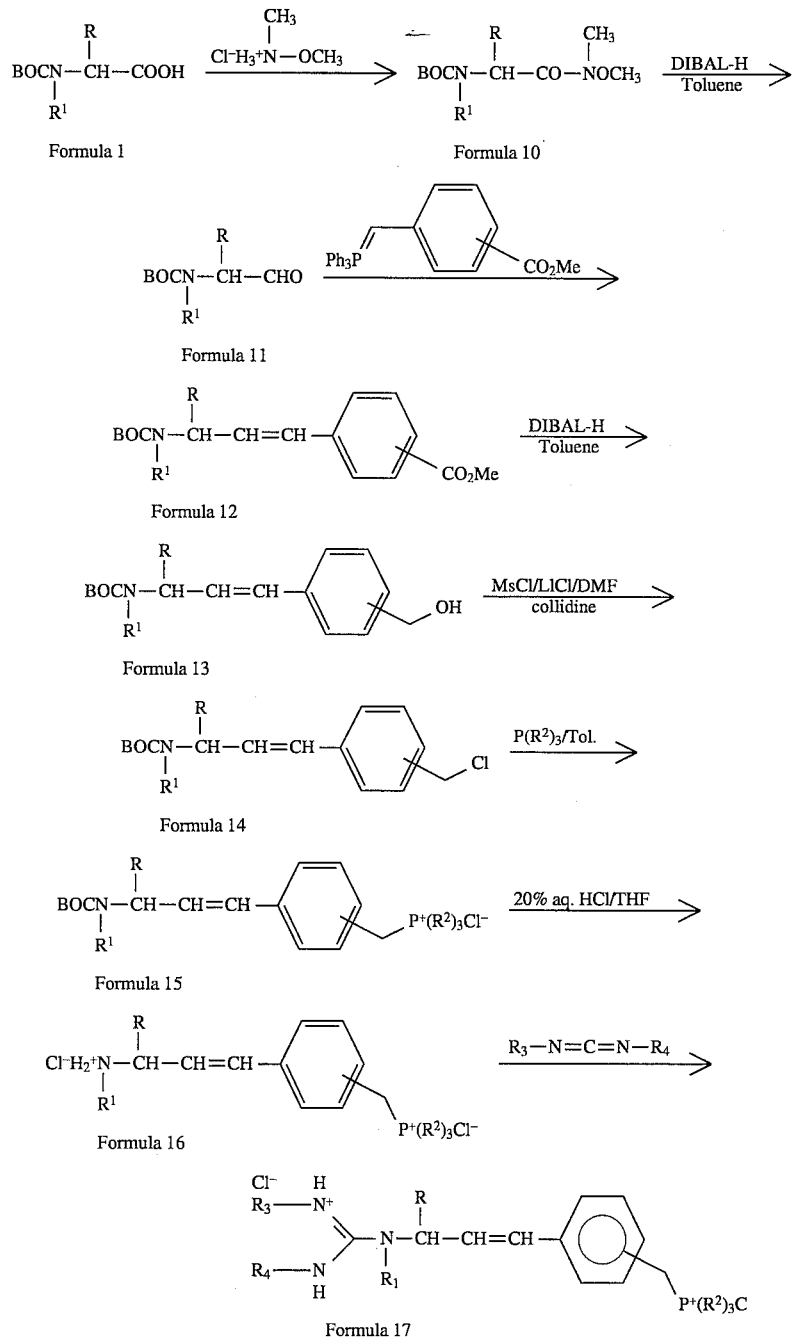

wherein
R is H, CH$_2$Ph, CH$_2$CH$_2$Ph,

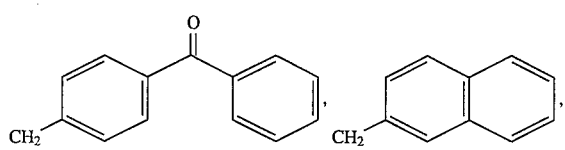

-continued
Scheme 3

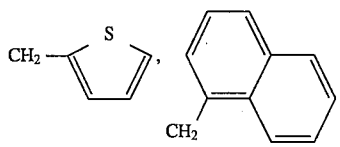

$R^1$ is H, alkyl;
DIBAL is diisobutylaluminumhydride;
$R^2$ is butyl, pentyl;
$R^3$ is cyclohexyl, isopropyl, propyl, $pCH_3C_6H_5$; and
$R^4$ is cyclohexyl, isopropyl, $CH_2CH_2CH_3PhpCH_3C_6H_5$ The following examples will further illustrate the synthesis of the compounds of the present invention.

It is to be noted that compounds of this invention may contain at least one asymmetric carbon atom. As a result, compounds of Formulae I and II may be obtained either as racemic mixtures or as individual enantiomers. When two asymmetric centers are present, the product may exist as a mixture of two diasteromers.

EXAMPLE 1

Phosphonium,
[[4-[[2-[[bis(cyclohexylamino)methylene]amino]-3-(2-naphthalenyl)-1-oxopropyl]amino]phenyl]methyl]
tributyl-, chloride,monohydrochloride

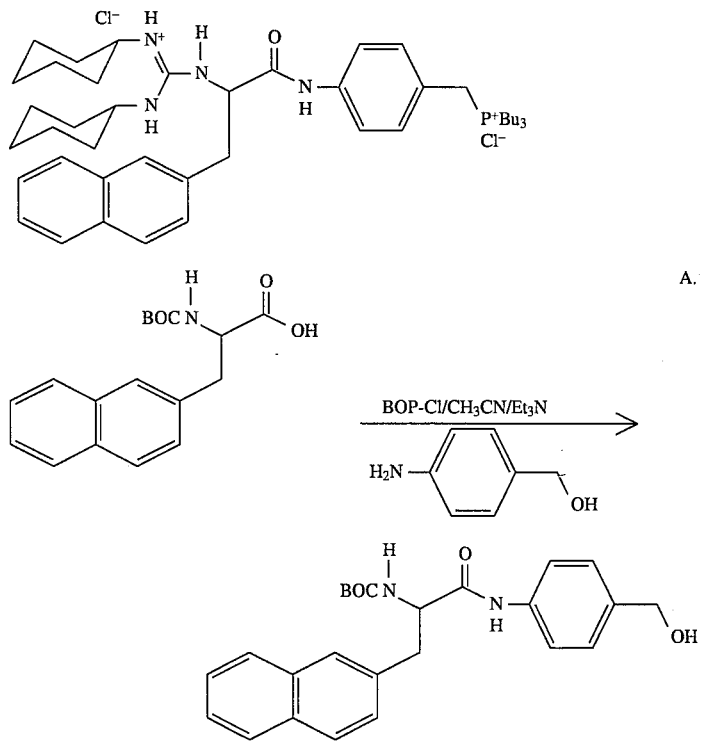

N-tert-Butyloxycarbonyl-β-(2-naphthyl)-alanine(7.3 gm; 23.2 mmol) was dissolved in anhydrous acetonitrile (150 ml) and cooled to 0° C. over an ice bath. Then bis(2-oxo-3-oxazolidinyl)phosphinic chloride (BOP-Cl; 8.8 gm; 34.8 mmol) was added in one portion, followed by dropwise addition of triethylamine (9.7 ml; 69.6 mmol) over 15 minutes. The reaction mixture was warmed to room temperature and stirred for 30 minutes. Then 4-aminobenzyl alcohol (5.7 gm; 46.4 mmol) was added to the reaction mixture at room temperature, and the reaction was stirred for 2 days. The reaction mixture was concentrated in vacuo on a rotoevaporator, the residue was dissolved in 300 ml of ethyl acetate and washed with water (2×150 ml), 5% aq HCl solution (1×150 ml), water (1×150 ml), then saturated aqueous sodium chloride solution (1×50 ml). The organic layer was dried over $MgSO_4$ then evaporated and the residue purified by flash chromatography (20% EtOAc in hexanes) to yield product.

A.

B.

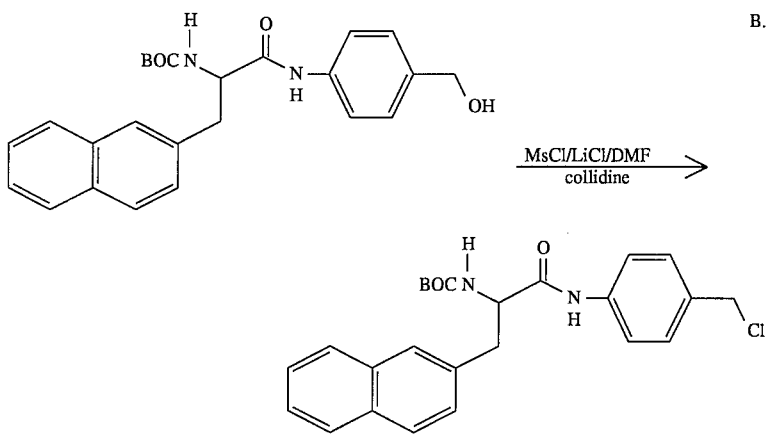

The intermediate compound (1.3 gm; 3.0 mmol) was dissolved in anhydrous DMF (20 ml) containing collidine (0.94 ml; 7.2 mmol). The reaction mixture was cooled to 0° C. over an ice bath, and methane sulfonyl chloride (0.36 ml; 4.68 mmol) was added followed by the addition of anhydrous lithium chloride(1.5 gm; 36 mmol). The reaction mixture was warmed to room temperature and magnetically stirred for 2.5 hours, monitoring the disappearance of starting material by thin layer chromatography on silica (tlc) ($RF_{sm}$=0.3; $Rf_{prd}$=0.7; 30% EtOAc in hexanes). The reaction mixture was then diluted with 800 ml of ethyl acetate and washed with $H_2O$ (1×150 ml); cold 5% aqueous HCl solution (1×150 ml), $H_2O$ (2×150 ml); saturated aqueous sodium bicarbonate solution (1×150 ml), $H_2O$ (1×150 ml) and saturated aqueous sodium chloride solution (1×50 ml). The organic layer was dried over anhydrous $MgSO_4$ and rotoevaporated. The residue was purified by flash chromatography (10% ethyl acetate in hexanes) to yield the benzyl chloride product.

C.

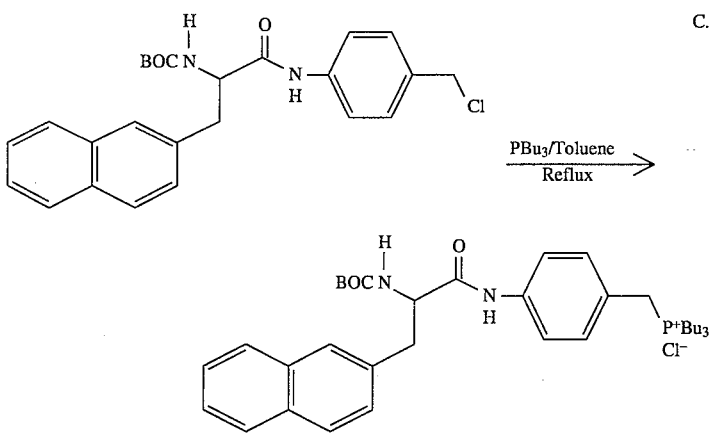

The benzyl chloride intermediate (1.25 gm; 2.8 mmol) was dissolved in anhydrous toluene (25 ml). Tributylphosphine (3.5 ml; 14.2 mmol) was added to the solution and the reaction mixture was heated to reflux for eight hours. The reaction mixture was triturated with hexane and the resulting white precipitate filtered to yield the tributyl phosphonium salt.

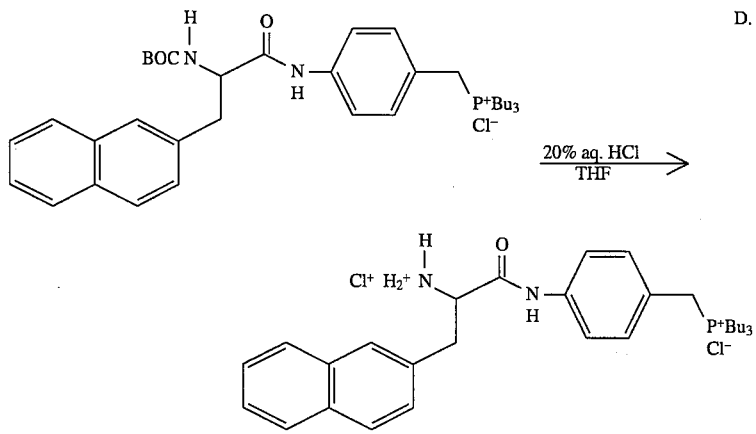

D.

The N-Boc derivative (140 mg; 0.22 ml) was dissolved in THF and 20% aqueous HCl was added to the solution. The reaction mixture was stirred at room temperature overnight, evaporation of the solvent gave the amine hydrochloride salt.

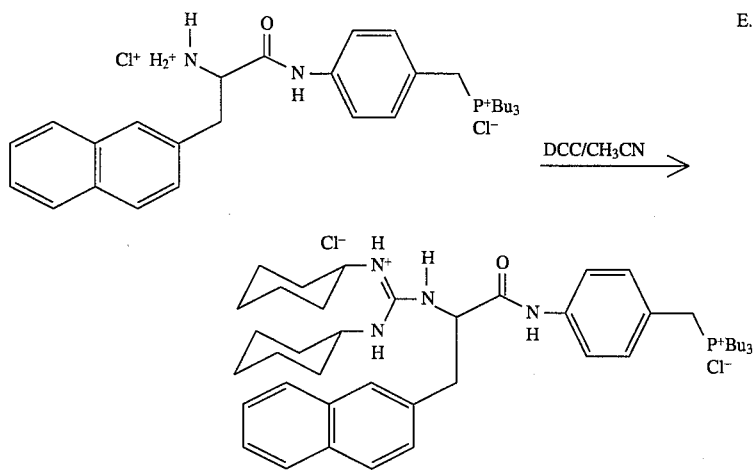

E.

The amine hydrochloride salt (175 mg; 0.3 mmol) was combined with N,N'-dicyclohexylcarbodiimide (DCC; 311 mg; 1.5 mmol) in 15 ml of anhydrous acetonitrite. The reaction mixture was stirred at room temperature for 48 hours after which the solvent was removed in vacuo by rotoevaporation. The residue was then triturated with diethyl ether and filtered. The precipitate was washed with hot ethyl acetate several times to remove N,N'-dicyclohexyl urea. The precipitate was dried at 45° C. in a vacuum oven to yield the pure guanidine, Phosphonium, [[4-[[2-[[bis(cyclohexylamino )methylene]amino]-3-(2-naphthalenyl)-1-oxopropyl]amino]phenyl]methyl]tributyl-, chloride, monohydrochloride, as a monohydrate.

C, H, N calculated for $C_{45}H_{68}ON_4PCl \cdot HCl \cdot H_2O$ Calc. %C=67.40 %H=8.92 %N=6.99 Found %C=67.14 %H=8.75 %N=6.94 Mass spectra: m/z=712 for $[M-HCl-Cl^-]^+$

EXAMPLE 2

Phosphonium[[4-[[2-[[bis(cyclohexylamin)methylene]amino]-1-oxo-3-phenylpropyl]amino]phenyl]methyl] tributylchloride, monohydrochloride

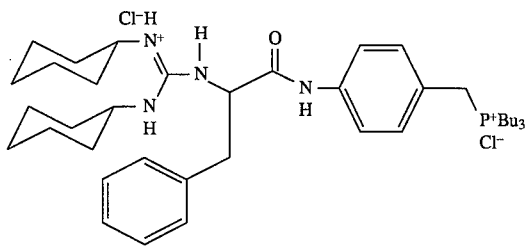

L and D isomers

Synthesis of phosphonium[[4-[[2-[[bis(cydohexylamin) methylene]amino]-1-oxo-3-phenylpropyl]amino]phenyl] methyl]tributylchloride, monohydrochloride were accomplished according to Scheme 1 starting from commercially available N-BOC-phenylalanine as Formula 1.

R=CH$_2$Ph, R$^1$=Butyl, R$^3$=R$^4$=cyclohexyl. C, H, N calculated for C$_{41}$H$_{66}$ON$_4$PCl.HCl.H$_2$O  Calc. %C=65.49 %H=9.25 %N=7.45 Found %C=65.65 %H=9.27 %N=7.45

EXAMPLE 3

Phosphonium, [[4-[[3-(4-benzoylphenyl)-2-[[bis(cyclohexylamino)methylene]amino]-1-oxopropyl]amino]phenyl]methyl]tributyl-, chloride, monohydrochloride

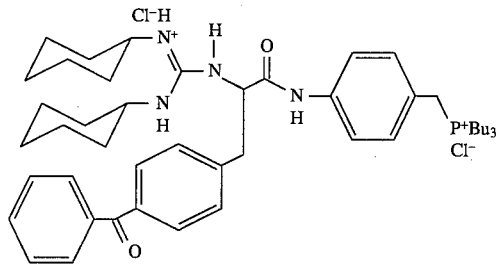

Synthesis of Phosphonium, [[4-[[3-(4-benzoylphenyl)-2-[[bis(cyclohexylamino)methylene]amino]-1-oxopropyl]amino]phenyl]methyl]tributyl, chloride, monohydrochloride was accomplished according to Scheme 1 starting from N-BOC-p-(benzyol)phenylalanine as in Formula 1. N-BOC-p-(benzoyl)phenylalanine was prepared according to the procedures described in: Kauer, J. C. U.S. Pat. No. 4,762,881. J. C. Kauer, S. Erickson-Viitaneu, H. R. Wolfe, Jr., and W. F. DeGrado; *J. Biol. Chem.* (1986), 261, 10695.

R=

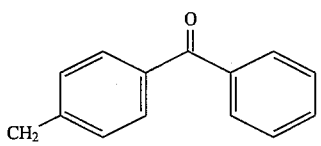

R$^1$=H; R$^2$=Butyl; R$^3$=R$^4$=cyclohexyl C, H, N calculated for C$_{48}$H$_{70}$O2N$_4$PCl.HCl.1.5 H$_2$O Calc. %C=66.65 %H=8.62 %N=6.48 Found %C=66.69 %H=8.30 %N=6.37

EXAMPLE 4

Phosphonium, [[4-[[2-[bis(2-methylethylamino)methylene]amino]-3-(2-naphthalenyl)-1-oxopropyl]amino]phenyl]methyl]tributyl-, chloride, monohydrochloride

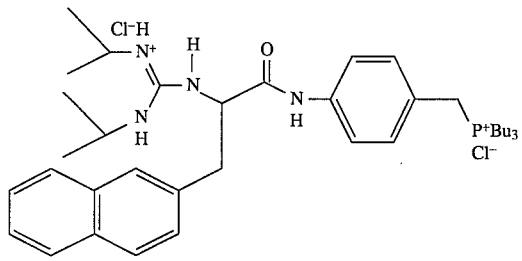

Preparation of Phosphonium, [[4-[[2-[bis(2-methylethylamino)methylene]amino]-3-(2 -naphthalenyl)-1-oxopropyl]amino]phenyl]methyl]tributyl-, chloride, monohydrochloride was accomplished according to Scheme 1 starting from N-BOC-β-(2-naphthyl)alanine as Formula I.

R=

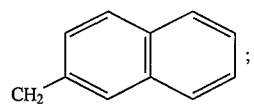

R$^1$=H; R$^2$=Butyl; R$^3$=R$^4$=isopropyl C, H, N calculated for C$_{39}$H$_{60}$ON$_4$PCl.HCl.H$_2$O  Calc. %C=64.89 %H=8.80 %N=7.76 Found %C=64.92 %H=8.44 %N=7.65

EXAMPLE 5

Phosphonium, [[4-[[2-[[bis(cyclohexylamino)methylene]amino]-3-(2-naphthalenyl)-1-oxopropyl]amino]phenyl]methyl]tributyl-, chloride, monohydrochloride

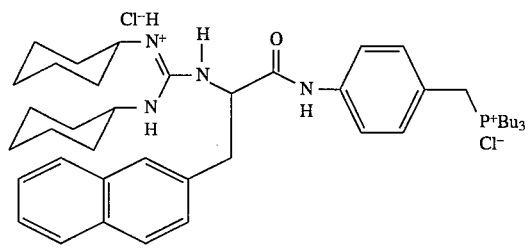

Preparation of Phosphonium, [[4-[[2-[[bis(cyclohexylamino)methylene]amino]-3-(2-naphthalenyl)-1-oxopropyl]amino]phenyl]methyl]tributyl-, chloride, monohydrochloride was accomplished according to Scheme 1 starting from N-BOC-β-(2-naphthyl)alanine as Formula 1.

R=

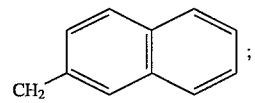

R$^1$=H; R$^2$=Butyl; R$^3$=R$^4$=cyclohexyl. C, H, N calculated for C$_{45}$H$_{68}$ON$_4$PCl.HCl.H$_2$O  Calc. %C=67.40 %H=8.92 %N=6.99 Found %C=67.14 %H=8.75 %N=6.94 Mass spectra: m/z=712 for [M–HCl–Cl$^-$]$^+$

EXAMPLE 6

Phosphonium, [[4-[[2-[[bis(cyclohexylamino)methylene]amino]-3-(2-naphthalenyl)-1-oxopropyl]amino]phenyl]methyl]tripentyl-, chloride, monohydrochloride

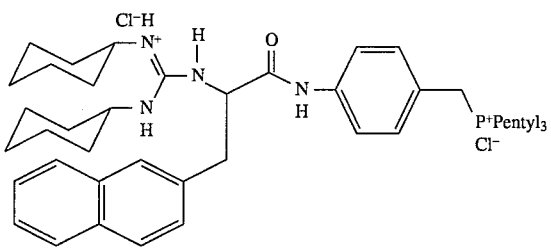

L and D isomers

Preparation of Phosphonium, [[4-[[2-[[bis(cyclohexylamino)methylene]amino]-3-(2-naphthalenyl)-1-oxopropyl]amino]phenyl]methyl]tripentyl-, chloride, monohydrochloride was accomplished according to Scheme 1 starting from N-BOC-β-(2-naphtyl)alanine as in Formula 1.

R=

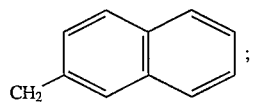

$R^1$=H; $R^2$=pentyl; $R^3$-cyclohexyl C, H, N calculated for $C_{48}H_{74}ON_4PCl \cdot HCl$ Calc. %C=69.80 %H=9.15 %N=6.78 Found %C=69.41 %H=9.20 %N=6.69 Mass spectra: m/z=754 for $[M-HCl-Cl^-]^+$

EXAMPLE 7

Phosphonium, [[4-[[2-[[bis(cyclohexylamino)methylene]amino]-1-oxo-3-(2-thienyl)propyl]amino]phenyl]methyl]tributyl-, chloride, monohydrochloride

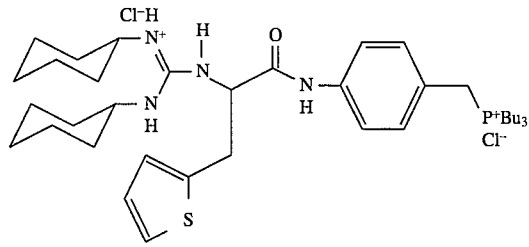

Preparation of Phosphonium, [[4-[[2-[[bis(cyclohexylamino)methylene]amino]-1-oxo-3-(2-thienyl)propyl]amino]phenyl]methyl]tributyl-, chloride, monohydrochloride was accomplished according to Scheme 1 starting from N-BOC-β-(thienyl)-alanine as Formula I.

R=

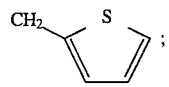

$R^1$=H; $R^2$=butyl; $R^3=R^4$=cyclohexyl. C, H, N calculated for $C_{39}H_{64}ON_4PSCl \cdot HCl$ Calc. %C=63.31 %H=8.85 %N=7.57 Found %C=63.31 %H=8.87 %N=7.46 Mass spectra: m/z=667 for $[M-HCl-Cl^-]^+$

EXAMPLE 8

Phosphonium, [[4-[[2-[[bis(cyclohexylamino)methyleneamino]-3-(2-naphthalenyl)-1-oxopropyl]amino]phenyl]methyl]triphenyl-, chloride,monohydrochloride

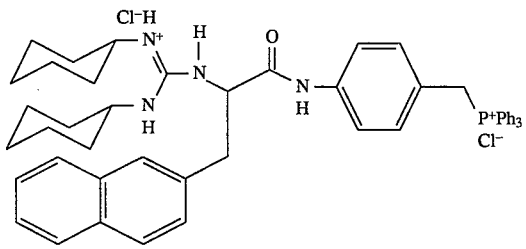

Preparation of Phosphonium, [[4-[[2-[[bis(cyclohexylamino)methyleneamino]-3-(2-naphthalenyl)-1-oxopropyl]amino]phenyl]methyl]triphenyl-, chloride,monohydrochloride was accomplished according to Scheme 1 starting from N-BOC-β-(2-naphtyl)alanine as Formula 1.

R=

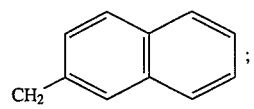

$R^1$=H; $R^2$=phenyl; $R^3=R^4$=cyclohexyl C, H, N calculated for $C_{51}H_{56}ON_4PCl \cdot HCl \cdot 1.25\ H_2O$ Calc. %C=70.70 %H=6.92 %N=6.47 Found %C=70.56 %H=7.07 %N=6.56 Mass spectra: m/z=771 for $[M-HCl-Cl^-]^+$

EXAMPLE 9

Phosphonium, [[4-[[2-[[bis(cyclohexylamino)methylene]amino]-3-(1-naphthalenyl)-1-oxopropyl]amino]phenyl]methyl]tributyl-, chloride, monohydrochloride

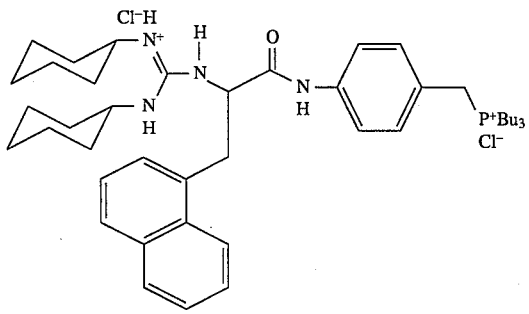

Preparation of Phosphonium, [[4-[[2-[[bis(cyclohexylamino)methylene]amino]-3-(1-naphthalenyl)-1-oxopropyl]amino]phenyl]methyl]tributyl-, chloride, monohydrochloride was accomplished according to Scheme 1 starting from N-BOC-β-(1-naphthyl)-alanine as Formula 1.

R=

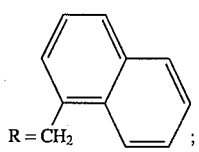

R = CH₂ ;

$R^1$=H; $R^2$=butyl; $R^3$=$R^4$=cyclohexyl C, H, N calculated for $C_{45}H_{68}ON_4PCl.HCl.H_2O$ Calc. %C=67.40 %H=8.92 %N=6.99 Found %C=67.28 %H=8.93 %N=7.08 Mass spectra: m/z=712 for [M–HCl–Cl⁻]⁺

EXAMPLE 10

Phosphonium,
tributyl[[4-[[3-(2-naphthalenyl)-1-oxo-2-[[[(3-phenylpropyl)amino](propylamino)methylene]amino]propyl]amino]phenyl]methyl]-, chloride, monohydrochloride

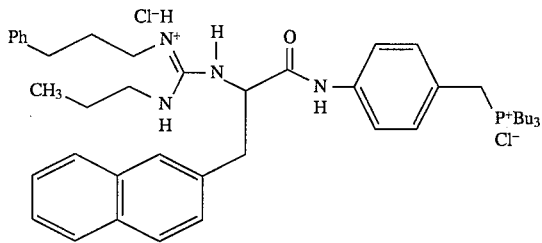

Preparation of Phosphonium, tributyl[[4-[[3-(2-naphthalenyl)-1-oxo-2-[[[(3-phenylpropyl)amino](propylamino)methylene]amino]propyl]amino]phenyl]methyl]-, chloride, monohydrochloride was accomplished according to Scheme 1, the novel carbodiimide used in converting Formula 5 to 6 was prepared from the thiourea following literature procedure of.

O. Mitsunobu, K. Kato and M. Tomari; *Tetrahedron* (1970), 26, 5731.

R=

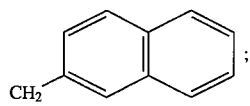

$R^1$=H; $R^2$=butyl; $R^3$=propyl; $R^4$=CH₂CH₂CH₂Ph C, H, N calculated for $C_{45}H_{64}ON_4PCl.HCl.H_2O$ Calc. %C=67.74 %H=8.46 %N=7.02 Found %C=68.29 %H=8.47 %N=7.02 Mass spectra: m/z=708 for [M–HCl–Cl⁻+H]⁺

EXAMPLE 11

Phosphonium,
[[4-[[2-[[bis(cyclohexylamino)methylene]N-methylamino]-3-(2-naphthalenyl)-1-oxopropyl]amino]phenyl]methyl]tributyl-, chloride, monohydrochloride

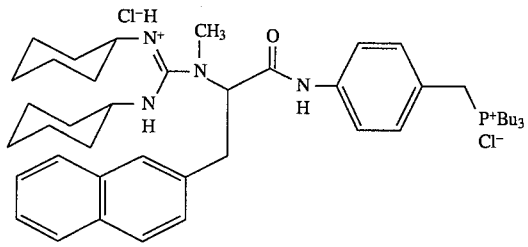

Preparation of Phosphonium, [[4-[[2-[[bis(cyclohexylamino)methylene] N-methylamino]-3-(2-naphthalenyl)-1-oxopropyl]amino]phenyl]methyl]tributyl-, chloride, monohydrochloride was accomplished according to Scheme 1 starting from N-BOC-β-(2-naphthyl)-alanine as in Formula 1.

N-methyl-N-BOC-β-(2-naphthyl)-alanine was prepared by N alkylation of N-BOC-β-(2-naphthyl)-alanine with methyl iodide.

R=

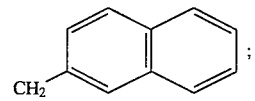

$R^1$=CH₃; $R^2$=butyl; $R^3$=$R^4$=cyclohexyl C, H, N calculated for $C_{46}H_{70}ON_4PCl.HCl.3H_2O$ Calc. %C=64.85 %H=9.11 %N=6.58 Found %C=64.76 %H=9.06 %N=5.88 Mass spectra: m/z=726 for [M–HCl–Cl⁻]⁺

EXAMPLE 12

Phosphonium,
[[4-[[2-[[bis[(4-methylphenyl)amino]methylene]amino]-3-(2-naphthalenyl)-1-oxopropyl]amino]phenyl]methyl]tributyl-, chloride, monohydrochloride

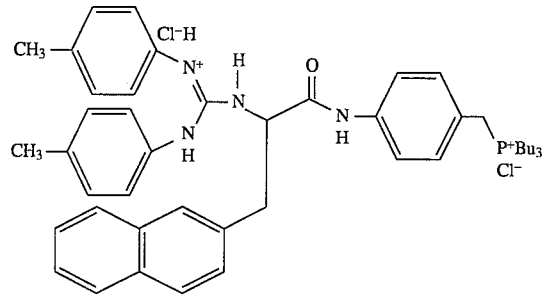

Preparation of Phosphonium, [[4-[[2-[[bis[(4-methylphenyl)amino]methylene]amino]-3-(2-naphthalenyl)-oxopropyl]amino]phenyl]methyl]tributyl-, chloride, monohydrochloride was accomplished according to Scheme 1. Commercially available N,N'-ditolylcarbodiimide was used for conversion of Formula 5 to Formula 6. Reaction mixture was heated at 60° C. for 5 hours.

R=

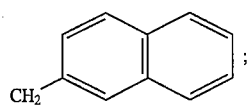

$R^1$=H; $R^3$=$R^4$=p$CH_3C_6H_5$ C, H, N calculated for $C_{47}H_{60}ON_4PCl\cdot HCl\cdot H_2O$ Calc. %C=69.02 %H=7.76 %N=6.85 Found %C=69.00 %H=7.72 %N=7.05 Mass spectra: m/z=727 for $[M-HCl-Cl^-]^+$

EXAMPLE 13

Phosphonium, [[4-[[3-benzo[b]thien-3-yl-2-[[bis(cyclohexylamino) methylene]amino]-1-oxopropyl]amino]phenyl]methyl] tributyl-, chloride, monohydrochloride

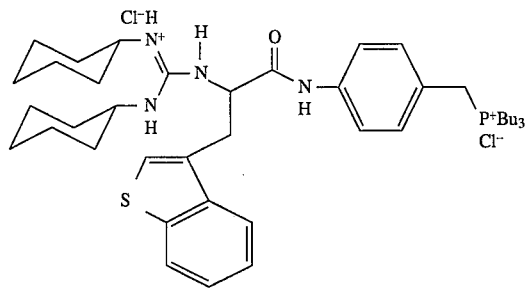

Preparation of Phosphonium, [[4-[[3-benzo[b]thien-3-yl-2-[[bis(cyclohexylamino)methylene]amino]-1-oxopropyl] amino]phenyl]methyl]tributyl-, chloride, monohydrochloride was accomplished according to Scheme 1 starting from N-BOC-β-(benzthienyl)alanine as in Formula 1.

R=

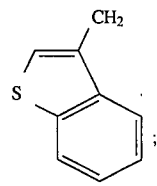

$R^1$=H; $R^2$=Butyl; $R^3$=$R^4$=cyclohexyl. C, H, N calculated for $C_{43}H_{66}ON_4PSCl\cdot HCl\cdot 0.5\ H_2O$ Calc. %C=64.64 %H=8.58 %N=7.01 Found %C=64.49 %H=8.57 %N=6.98 64.11 8.49 Mass spectra: m/z=717 for $[M-HCl-Cl^-]^+$

EXAMPLE 14

Phosphonium, [[4-[[2-[[bis(cyclohexylamino)methylene]amino]-1-oxo-4-phenylbutyl]amino]phenyl]methyl]tributyl-, chloride, monohydrochloride

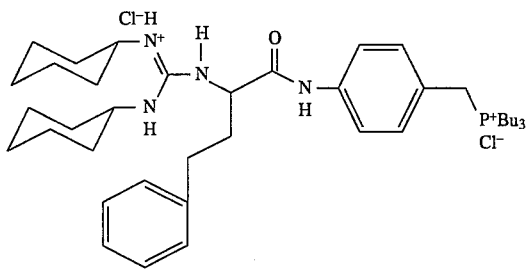

Preparation of Phosphonium, [[4-[[2-[[bis(cyclohexylamino)methylene]amino]-1-oxo-4-phenylbutyl]amino]phenyl]methyl]tributyl-, chloride, monohydrochloride was accomplished according to Scheme 1 starting from N-BOC-homophenyl alanine as Formula 1.

R=$CH_2CH_2Ph$; $R^1$=H; $R^2$=butyl; $R^3$=$R^4$=cyclohexyl C, H, N calculated for $C_{42}H_{68}ON_4PCl\cdot HCl\cdot 1.5\ H_2O$ Calc. %C=65.10 %H=8.98 %N=7.21 Found %C=65.18 %H=9.18 %N=7.02 Mass spectra: m/z=675 for $[M-HCl-Cl^-]^+$

EXAMPLE 15

Phosphonium, [[4-[[2-[[bis(cyclohexylamino)methylene]amino]-3-(1H-indol-3-yl)-1-oxopropyl]amino]phenyl]methyl]tributyl-, chloride, monohydrochloride

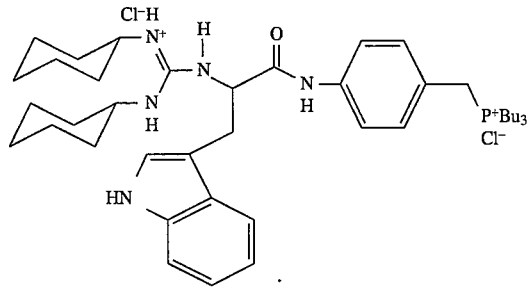

Preparation of Phosphonium, [[4-[[2-[[bis(cyclohexylamino)methylene]amino]-3-(1H-indol-3-yl)-1-oxopropyl] amino]phenyl]methyl]tributyl-, chloride, monohydrochloride was accomplished according to Scheme 1 starting from N-BOC-$N^1$-formyl-tryptophan as in Formula 1.

R=

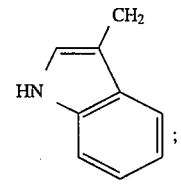

$R^1$=H; $R^2$=Butyl; $R^3$=$R^4$=cyclohexyl Deprotection of the N-BOC and $N^1$-formyl group occur simultaneosly under the reaction conditions in scheme 1 converting Formula 4 to Formula 5 i.e.:

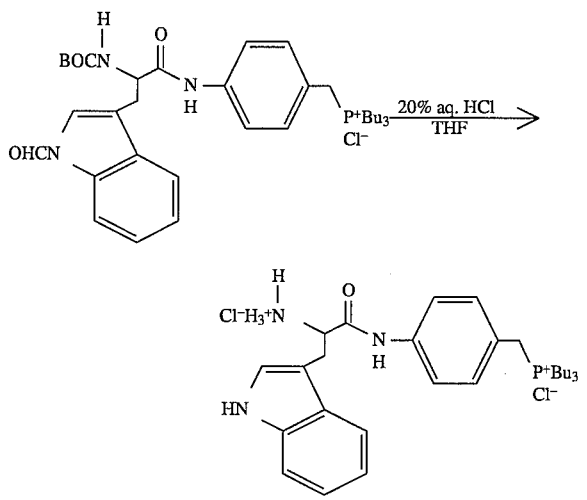

C, H, N calculated for $C_{43}H_{67}ON_5PCl.HCl.2.5 H_2O$ Calc. %C=63.14 %H=9.00 %N=8.56 Found %C=63.40 %H=8.88 %N=8.61 Mass spectra: m/z=701 for $[M-HCl-Cl^-]^+$

EXAMPLE 16

Phosphonium, [[4-[[[[bis(cyclohexylamino)methylene]amino]-2-naphthalenylacetyl]amino]phenyl]methyl]tributyl-, chloride, monohydrochloride

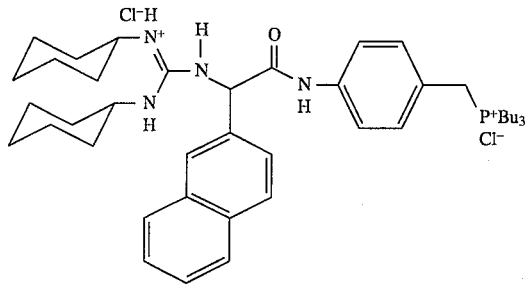

The N-BOC-(2-naphthyl)glycine was prepared according to:

U.S. Pat. No. 4,474,780, which is incorporated herein by reference.

Preparation of Phosphonium, [[4-[[[[bis(cyclohexylamino)methylene]amino]-2-naphthalenylacetyl]amino]phenyl]methyl]tributyl-, chloride, monohydrochloride was then completed according to Scheme 1 starting from N-BOC-(2-naphthyl)glycine as Formula 1.

R=

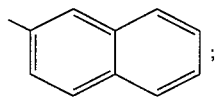

$R^1$=H; $R^2$=Butyl; $R^3$=$R^4$=cyclohexyl C, H, N calculated for $C_{44}H_{66}ON_4PCl.HCl.2 H_2O$ Calc. %C=65.57 %H=8.88 %N=6.95 Found %C=65.40 %H=8.87 %N=6.88 Mass spectra: m/z=697 for $[M-HCl-Cl^-]^+$

EXAMPLE 17

Phosphonium, [[3-[[2-[[bis(cyclohexylamino)methylene]amino]-3-(2-naphthalenyl)-1-oxopropyl]amino]phenyl]methyl] tributyl-, chloride, monohydrochloride

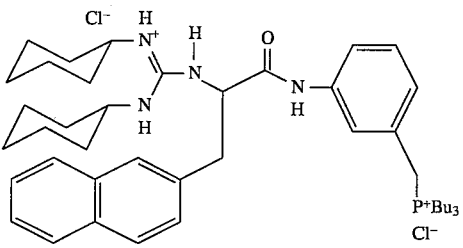

Preparation of Phosphonium, [[3-[[2-[[bis(cyclohexylamino)methylene]amino]-3-(2-naphthalenyl)-1-oxopropyl] amino]phenyl]methyl]tributyl-, chloride, monohydrochloride was accomplished according to Scheme 1 starting from N-BOC-β-(2-naphthyl)-alanine as in Formula 1, and coupling with 3-amino-benzyl alcohol. Mass spectra calculated for $C_{45}H_{68}ON_4PCl.HCl$ m/z=712 for $[M-HCl-Cl^-]^+$

EXAMPLE 18

2-Naphthalenepropanamide, N-1-azabicyclo[2.2.2]oct-3-yl-α-[[bis(cyclohexylamino)methylene]amino]-dihydrochloride

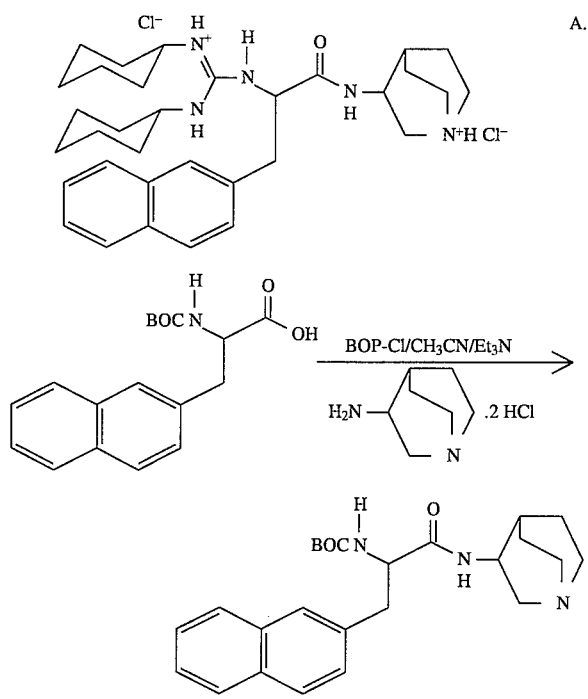

N-Boc-β-(2-naphthyl)alanine (231.0 mg; 0.67 mmol) was dissolved in anhydrous acetonitrile. The reaction mixture was cooled over an ice bath and bis(2-oxo-3-oxazolidinyl)phosphinic chloride (BOP-Cl; 203.6 mg; 0.8 mmol) was added, followed by dropwise addition of triethylamine (0.5 ml; 3.3 mmol). The reaction mixture was stirred at 0° C. for 15 minutes, then 3-aminoquinuclidine dihydrochloride (159 mg; 0.8 mmol) was added to the reaction mixture. The solution was warmed to room temperature and stirred for four hours. The reaction mixture was concentrated on a rotoevaporator and purified by flash chromatography silica (10 % MeOH in $CH_2Cl_2$) to yield the amide product.

B.

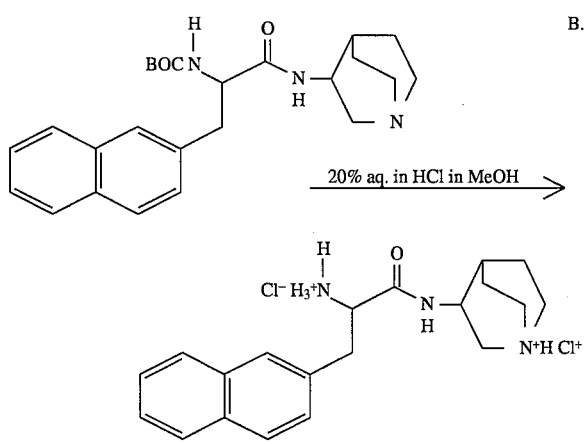

The N-BOC starting material (200 mg; 0.47 mmol) was dissolved in 10 ml of methanol, followed by the addition of 20 % aqueous HCl solution (5 ml). The reaction was stirred at room temperature for 6 hours then concentrated on a rotoevaporator. Trituration of the residue with 50 % diethyl ether in hexane yielded the dihydrochloride salt as a hydroscopic precipitate.

C.

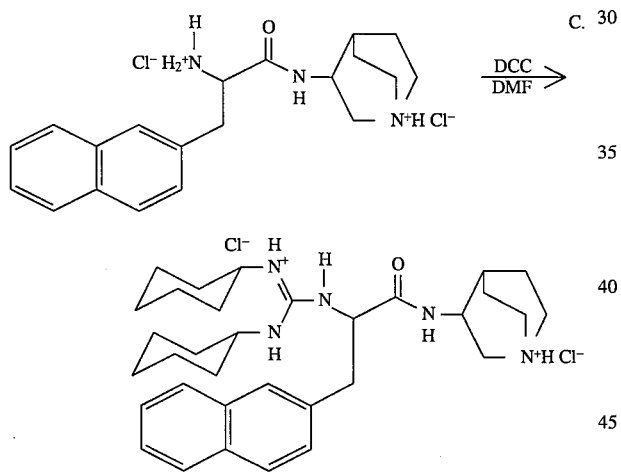

The hydrochloride salt (103 mg; 0.26 mmol) was dissolved in anhydrous DMF (5 ml) and combined with N,N'-dicyclohexylcarbodiimide (600 mg; 2.9 mmol). The reaction mixture was stirred at room temperature for 5 days after which the reaction was diluted with 50 % EtOAc in hexane. The precipitate was filtered and washed with hot ethyl acetate to yield pure product.

D.

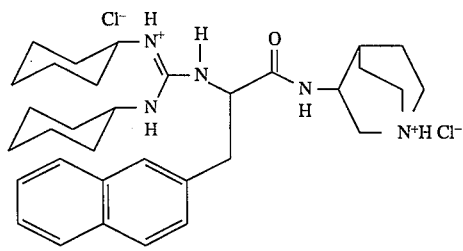

Preparation of 2-Naphthalenepropanamide, N-1-azabicyclo[2.2.2]oct-3-yl-α-[[bis(cyclohexylamino)methylene] amino]-dihydrochloride was accomplished according to Scheme 2N-BOC-β-(2-naphthyl)alanine as in Formula 1 and 3-amino quinuclidine dihydrochloride.

R=

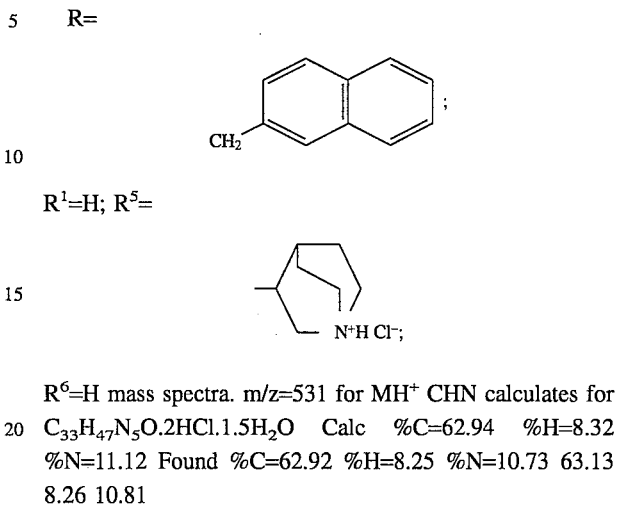

$R^1$=H; $R^5$=

$R^6$=H mass spectra. m/z=531 for $MH^+$ CHN calculates for $C_{33}H_{47}N_5O.2HCl.1.5H_2O$ Calc %C=62.94 %H=8.32 %N=11.12 Found %C=62.92 %H=8.25 %N=10.73 63.13 8.26 10.81

EXAMPLE 19

2-Naphthalenepropanamide, α-[[bis(cyclohexylamino)methylene]amino]-N-[4-(hydroxymethyl)phenyl]-, monohydrochloride

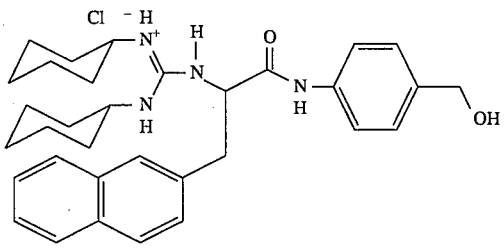

Preparation of 2-Naphthalenepropanamide, α-[[bis(cyclohexylamino)methylene]amino]-N-[4-(hydroxymethyl)phenyl]-, monohydrochloride was accomplished according to Scheme 2 with N-BOC-β-(2-naphthyl) alanine as in Formula 1 and 4-amino benzyl alcohol.

R=

$R^1$=H; $R^5$=

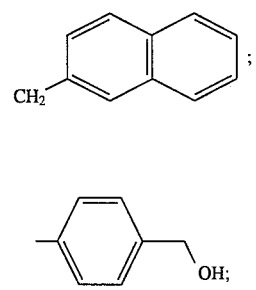

$R^6$=H mass spectra=M/Z=528 for $MH^+$ C, H, N calc for $C_{33}H_{42}N_4O_2.HCl.0.5H_2O$ Calc %C=69.27 %H=7.75 %N=9.79 Found %C=69.04 %H=7.53 %N=9/74

EXAMPLE 20

2-Naphthalenepropanamide, α-[[bis(cyclohexylamino)methylene]amino]-N-3-quinolinyl-, monohydrochloride

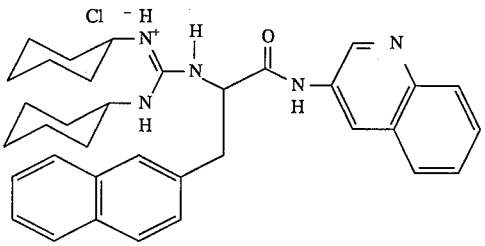

Preparation of 2-Naphthalenepropanamide, α-[[bis(cyclohexylamino)methylene]amino]-N-3-quinolinyl-, monohydrochloride was accomplished according to Scheme 2 with N-BOC-β-(2-naphthyl)alanine as in Formula 1 and 3-amino quinoline.

R=

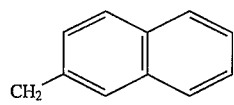

$R^1$=H $R^5$=

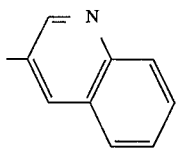

$R^6$=H Mass spectra M/Z=549 for $MH^+$ CHN calc for $C_{35}H_{41}N_5O.1HCl.H_2O$ Calc. %C=69.81 %10H=7.36 %N=11.63 Found %C=70.02 %H=7.33 %N=11.70

EXAMPLE 21

2-Naphthalenepropanamide, α-[[bis(cyclohexylamino)methylene]amino]-N-3-pyridinyl-, monohydrochloride

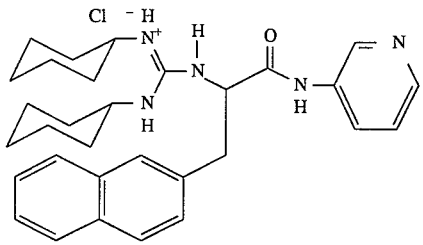

Preparation of 2-Naphthalenepropanamide, α-[[bis(cyclohexylamino)methylene]amino]-N-3-pyridinyl-, monohydrochloride was accomplished according to Scheme 2 with N-BOC-β-(2-naphthyl)alanine as Formula 1 and 3-amino pyridine.

R=

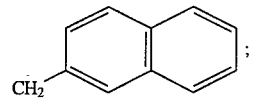

$R^1$=H; $R^5$=

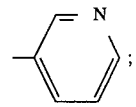

$R^6$=H Mass spectra m/z=498 for $M^+$ CHN calc for $C_{31}H_{39}N_5O.HCl.0.5\ H_2O$ Calc. %C=68.55 %H=7.61 %N=12.89 Found %C=68.80 %H=7.56 %N=12.40

EXAMPLE 22

4-chlorophenylpropanamide, N-1-azabicyclo[2.2.2]oct-3-yl-α-[[bis(cyclohexylamino)methylene]amino]-, dihydrochloride

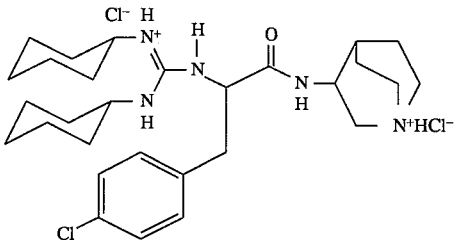

Preparation of 4-chlorophenylpropanamide, N-1-azabicyclo[2.2.2]oct-3 -yl-α-[[bis(cyclohexylamino)methylene]amino]-, dihydrochloride was accomplished according to Scheme 2 starting with N-BOC-p-chlorophenylalanine as in Formula 2 and 3-amino quinuclidine

R=

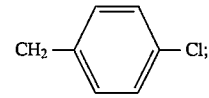

$R^1$=H; $R^5$=

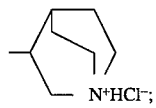

$R^6$=H Mass spectra m/z=514 for $M^+$

EXAMPLE 23

2-Naphthalenepropanamide,
N-1-azabicyclo[2.2.2]oct-3-yl-α-bis(cyclohexylamino)
methylene]amino]-N-(phenylmethyl)-,
dihydrochloride

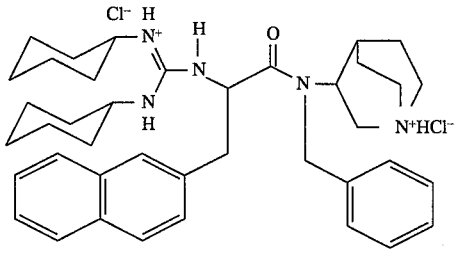

Preparation of 2-Naphthalenepropanamide, N-1-azabi-cyclo[2.2.2]oct-3-yl-α-[[bis(cyclohexylamino)methylene]amino]-N-(phenylmethyl)-, dihydrochloride was accomplished according to Scheme 2 from N-BOC-β(2-Naphthyl)alanine as in Formula 1 and 3-amino(N-benzyl)quinuclidine.

R=

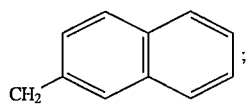

$R^1$=H.$R^5$=

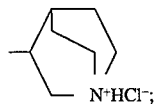

$R^6$=$CH_2Ph$ mass spectra m/z=621 for $MH^+$ CHN Calc. for $C_{40}H_{53}N5).2HCl.3H_2O$ Calc. %C=64.33 %H=8.23 %N=9.38 Found %C=64.22 %H=7.83 %N=9.20

EXAMPLE 24

2-Naphthalenepropanamide,
α-[[bis(cyclohexylamino)methylene]amino]-N-5-
isoquinolinyl-, monohydrochloride

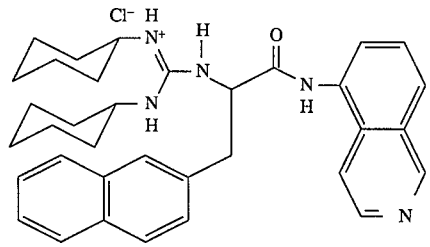

Preparation of 2-Naphthalenepropanamide, α-[[bis(cyclohexylamino)methylene]amino]-N-5-isoquinolinyl-, monohydrochloride was accomplished according to Scheme 2 starting from N-BOC-β(2-naphthyl)alanine as in Formulae 1 and 5-amino isoquinoline.

R=

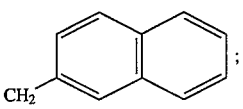

$R^1$=H.$R^5$=

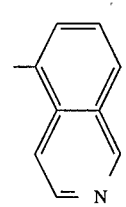

$R^6$=H mass spectra m/z=547 for $M^+$

EXAMPLE 25

2-Naphthalenepropanamide,
N-(1H-benzimidazol-2-ylmethyl)-α-[[bis
(cyclohexylamino)methylene]amino]-,
monohydrochloride

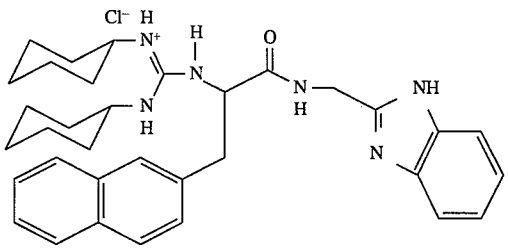

Preparation of 2-Naphthalenepropanamide, N-(1H-benzimidazol-2-ylmethyl)-α-[[bis(cyclohexylamino)methylene]amino]-, monohydrochloride was accomplished according to Scheme 2 starting from N-BOC-β(2-naphthyl)alaine as in Formulae 1 and 2-(amino methyl)benzimidazole dihydrochloride.

R=

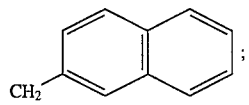

$R^1$=H.$R^5$=

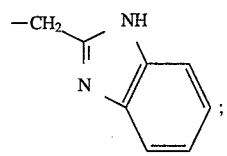

$R^6$=H Mass spectra M/Z=550 for $M^+$

The amide bond in Phosphonium, [[4-[[2-[[bis(cyclohexylamino)methylene]amino]-3-(2-naphthalenyl)-1-oxopropyl]amino]phenyl]methyl]tributyl-, chloride, monohydrochloride of Example 5 may be replaced by olefin as shown in the following Examples to obtain Phosphonium, [[4-[3-[[bis(cyclohexylamino)methylene]amino]-4-(2-naphthalenyl)-1-cis-butenyl]phenyl]methyl]tributyl-, chloride, monohydrochloride and Phosphonium, [[4-[3-[[bis(cyclohexylamino)methylene]amino]-4-(2-naphthalenyl)-1-trans-butenyl]phenyl]methyl]tributyl-, chloride, monohydrochloride.

EXAMPLE 26

Phosphonium, [[4-[3-[[bis(cyclohexylamino)methylene]amino]-4-(2-naphthalenyl)-1-cis-butenyl]phenyl]methyl]tributyl-, chloride, monohydrochloride and Phosphonium, [[4-[3-[[bis(cyclohexylamino)methylene]amino]-4-(2-naphthalenyl)-1-trans-butenyl]phenyl]methyl]tributyl-, chloride, monohydrochloride

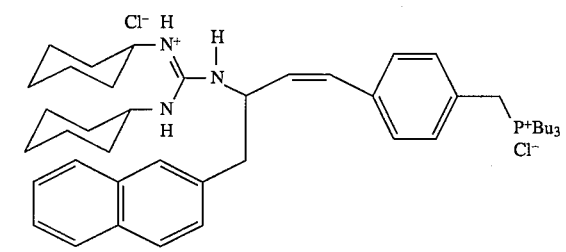

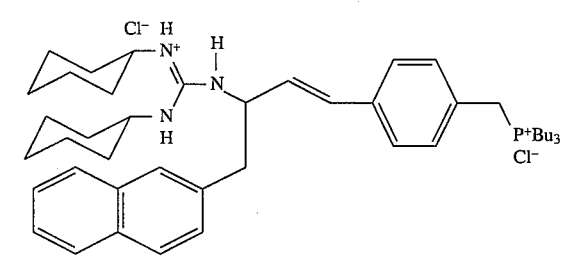

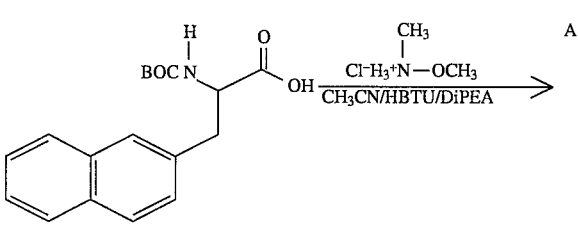

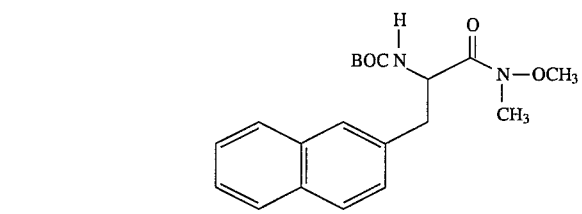

N-BOC-β-(2-naphthyl)alanine (5 gm; 15.8 mmol) was combined with O-benzotriazol-1-yl-N,N,N',N'-tetramethyl uronium hexafluoro-phosphate (HBTU; 9.02 gm; 23.3 mmol) and diisopropyl ethylamine (13.8 ml; 79.3 mmol) in anhydrous acetonitrile (50 ml). N,O-dimethyl hydroxylamine (1.5 gm; 15.8 mmol) was added to the reaction mixture and it was stirred at room temperature overnight under an argon atmosphere. The reaction mixture was concentrated on a rotoevaporator and diluted with ethyl acetate, then washed with $H_2O$ (3×500 ml) and saturated aqueous sodium chloride. The organic layer was dried over $MgSO_4$ and concentrated on a rotoevaporator. The residue was purified by flash chromatography (40% ethyl acetate in hexane) to give the desired product.

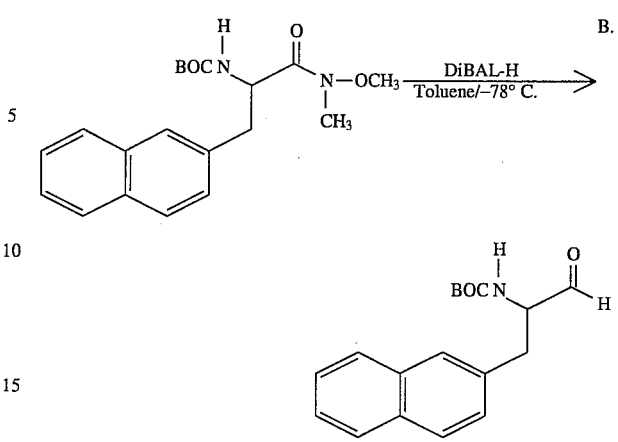

The Weinreb amide (1 gm. 2.8 mmol) was dissolved in anhydrous toluene (20 ml) and cooled to −78° C. (acetone/dry ice bath.) Diisobutylaluminium hydride (DiBAL-H; 1M in methylene chloride; 6 ml; 6 mmol) was added to the reaction mixture. The reaction mixture was stirred at −78° C. for 2 hours until the starting Weinreb amide disappeared by tlc analysis (40% EtOAc/hexane; Rf=0.2). The reaction was quenched by the addition of saturated aqueous Rochelle salt solution (2–3 ml) and stirred for 1 hour at room temperature. The reaction was dried over sodium sulfate and concentrated to give aldehyde which was used immediately without further purification.

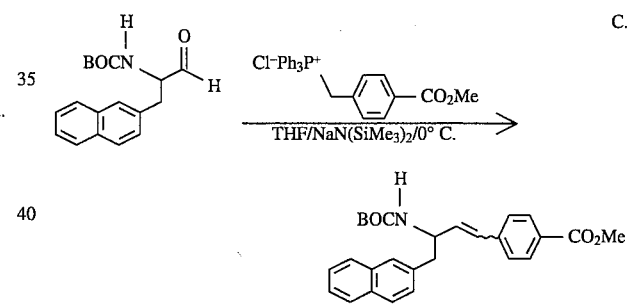

The phosphonium salt (1.25 gm; 1.79 ) was added to the THF (15 ml) and cooled to 0° C. Sodium hexamethyldisilazane (2.1 ml; 1.1 mmol; 1M in THF solution) was added to the reaction vessel and stirred at room temperature for 3 hours. The reaction was cooled to 0° C. and the aldehyde derived from N-BOC-β-(2naphthyl)alanine (0.60 gm; 2.0 mmol) was added to the reaction mixture. The solution was warmed to room temperature for 8 hours, after which the reaction was quenched by pouring the reaction mixture into a separatory funnel containing ethyl acetate (300 ml) and washing with $H_2O$ (3×200 ml). the organic layer was dried over $MgSO_4$ and evaporated to yield crude olefin as a brownish oil. This oil was purified by flash chromatography to give an inseparatable mixture of cis and trans olefins.

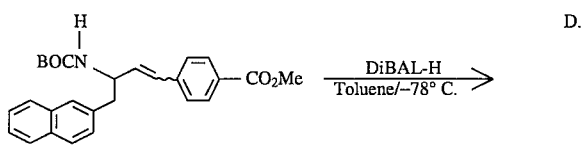

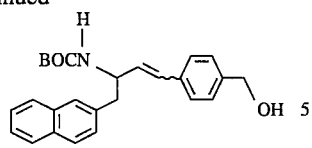

The methyl ester (0.67 gm; 1.56 mmol) was dissolved in anhydrous toluene and cooled to −78° C. DIBAL-H (1M in CH$_2$CH; 3.2 ml; 3.2 mmol) was added to the solution at −78° C. and the reaction mixture was stirred for 30 minutes at −78° C. The reaction was quenched with saturated aqueous Rochelle's salt solution (1–2 ml) diluted with ethyl acetate and dried over sodium sulfate and filtered. The filtrate was evaporated to give a mixture of cis and trans benzylic alcohols (approximately 1:4; cis:trans ratio). The mixture of olefins was separated by flash chromatography (30% EtOAc in hexane) to give pure cis and pure trans olefin.

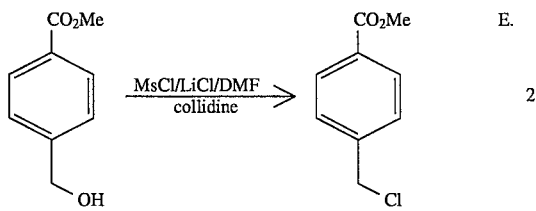

E.

Methyl (4-hydroxymethyl) benzoate (10 gm; 60.2 mmol) was dissolved in anhydrous DMF (600 ml) and cooled to 0° C. Collidine (79.5 ml; 601.7 mmol) was added to the reaction vessel followed by methane sulfonyl chloride (7 ml; 90.3 mmol). The reaction was stirred at 0° C. for 15 minutes, then anhydrous lithium chloride was added to the reaction mixture. The reaction was warmed to room temperature and stirred for 15 hours, after which the mixture was poured into a large separatory funnel and partitioned between ethyl acetate and H$_2$O. The organic layer was washed with 1N of HCl (2×300 ml), H$_2$O (3×300 ml) and saturated aqueous sodium chloride, then dried over MgSO$_4$, and concentrated to give an oil. The oil was purified by flash chromatography (20% EtOAc in hexane) to give the benzyl chloride as a colorless oil.

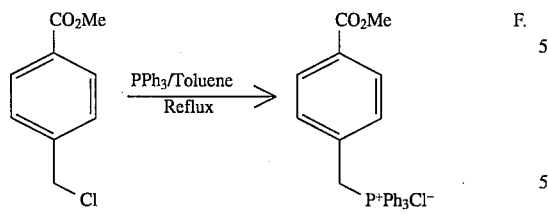

F.

Methyl (4-chloromethyl) benzoate (10.9 gm; 59.04 mmol) was combined with triphenylphosphine (15.4 gm; 59.04 mmol) in anhydrous toluene (100 ml). The mixture was heated to reflux for 16 hours, after which the mixture was cooled and the solvent decanted from the phosphonium salt. The salt was triturated with diethyl ether, then dissolved in 25% methanol in acetonitrile and filtered through silica gel. Evaporation of the solvent gave the phosphium salt as a white solid.

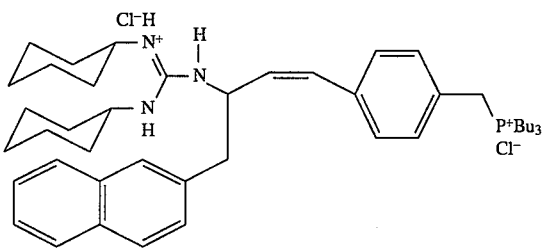

G.

The cis olefin benzylic alcohol was converted to Phosphonium, [[4-[3-[[bis(cyclohexylamino)methylene]amino]-4-(2-naphthalenyl)-1-cis-butenyl]phenyl]methyl]tributyl-, chloride, monohydrochloride according to Scheme 3. Cis benzyl alcohol is represented by Formulae 13 of Scheme 3 where the synthetic scheme parallels Scheme 1 Formula 2.

Mass spectra m/z=694.8 for [M−HCl−Cl−]$^+$ C, H, N for C$_{46}$H$_{69}$N$_3$PCl.HCl.1.2 H$_2$O Calc. %c=68.81 %H=9.29 %N=5.23 Found %c=68.81 %H=8.86 %N=5.45

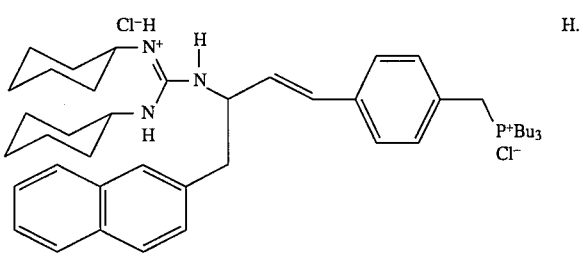

H.

The trans olefin benzylic alcohol was converted to Phosphonium, [[4-[3-[[bis(cyclohexylamino)methylene]amino]-4-(2-naphthalenyl)-1-trans-butenyl]phenyl]methyl]tributyl-, chloride, monohydrochloride according to Scheme 3 (Formula 13).

Mass spectra M/Z=694.8 for [M−HCl−Cl−]+ CHN calculated for C$_{46}$H$_{69}$N$_3$PCl.HCl.H$_2$O Calc %C=70.39 %H=9.25 %N=5.35 Found %C=70.23 %H=9.15 %N=5.41

Using the appropriate starting materials, the schemes and examples presented herein, other compounds according to the present invention may be made as well.

The receptor binding affinity (K$_I$) of the compounds of the present invention was determined in [$^3$H]-bradykinin radioligand binding studies using human IMR-90 fetal lung fibroblasts. These cells contain the bradykinin B$_2$ receptor as previously described (Sawutz et al, (1992) *Eur. J, Pharmacol., Mol. Pharmacol.*) which is incorporated herein by reference. Briefly stated, harvested IMR-90 cells were resuspended to the desired cell concentration in ice cold buffer containing phosphate buffered saline (PBS) pH-7.4, sodium azide (0.02%), 0.1% BSA, PMSF (1 mM), DTT (1 mM), and captopril (1 mM). For competitive inhibition binding studies, cells were incubated with bradykinin (1–2 nM) in the absence or presence of increasing concentrations of competing compound. All assay mixtures were incubated for 2 hours at 4° C. The binding assays were terminated by filtration through Whatman GF/B filters on a Brandel Cell Harvester and the filters were washed with 3×1 ml aliquots of ice cold PBS containing 0.1% BSA. All filters were presoaked in 0.1% polyethylenimine to decrease nonspecific filter binding.

The binding affinities (K$_I$) were calculated according to the method of Cheng and Prusoff, ((1973) *Biochem, Pharmacol.*, 22:2099), which is also incorporated herein by reference, using IC$_{50}$ values determined by EBDA (BioSoft, Inc.). The K$_D$ for [$^3$H] bradykinin used to calculate the K$_I$ values, determined in separate saturation binding experiments, was 2.1±0.2 nM. The data presented for each analog are mean values from 2-3 experiments.

Results are shown in Table I.

TABLE I

| Comp. of Example | Structure | IMR 90 Ki (μM) |
|---|---|---|
| 1 | 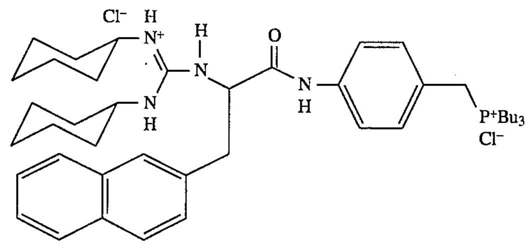 | 0.06<br>0.14 |
| 2 | 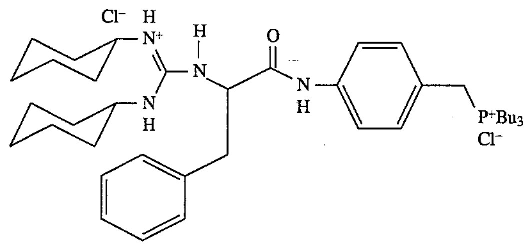 | 3.25<br>10.9 |
| 3 | 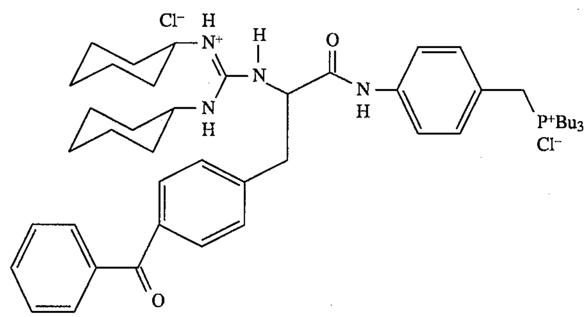 | 5.80 |
| 4 | 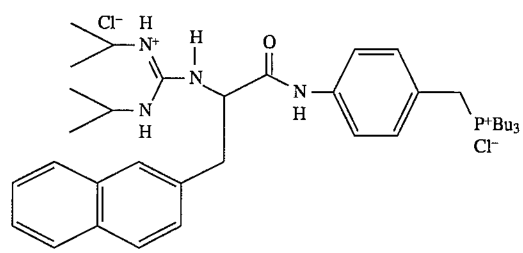 | 7.05 |
| 5 | 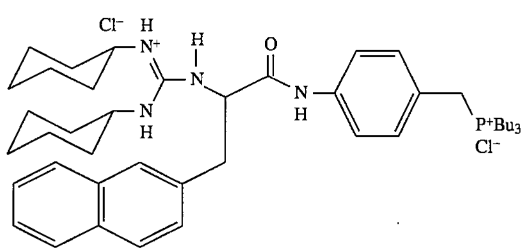 | 0.06<br>0.14 |

TABLE I-continued

| Comp. of Example | Structure | IMR 90 Ki (μM) |
|---|---|---|
| 6 | (dicyclohexyl guanidinium)-CH(CH₂-2-naphthyl)-C(O)NH-C₆H₄-CH₂-P⁺Pentyl₃ Cl⁻ | 0.06 / 0.31 |
| 7 | (dicyclohexyl guanidinium)-CH(CH₂-2-thienyl)-C(O)NH-C₆H₄-CH₂-P⁺Bu₃ Cl⁻ | 2.58 |
| 8 | (dicyclohexyl guanidinium)-CH(CH₂-2-naphthyl)-C(O)NH-C₆H₄-CH₂-P⁺Ph₃ Cl⁻ | 0.120 |
| 9 | (dicyclohexyl guanidinium)-CH(CH₂-1-naphthyl)-C(O)NH-C₆H₄-CH₂-P⁺Bu₃ Cl⁻ | 1.03 |
| 10 | (N-phenylpropyl, N'-propyl guanidinium)-CH(CH₂-2-naphthyl)-C(O)NH-C₆H₄-CH₂-P⁺Bu₃ Cl⁻ | 1.95 |
| 11 | (dicyclohexyl, N-methyl guanidinium)-CH(CH₂-2-naphthyl)-C(O)NH-C₆H₄-CH₂-P⁺Bu₃ Cl⁻ | 0.070 |

TABLE I-continued
| Comp. of Example | Structure | IMR 90 Ki (μM) |
|---|---|---|
| 12 | 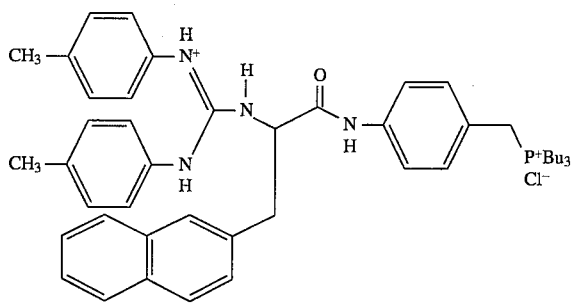 | 0.140 |
| 13 | 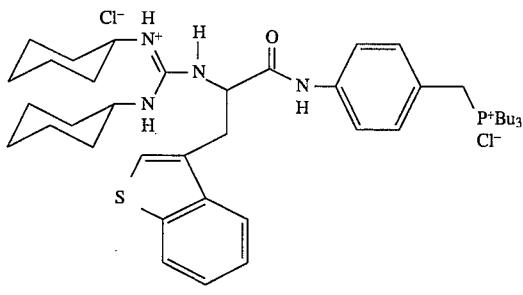 | 0.430 |
| 14 | 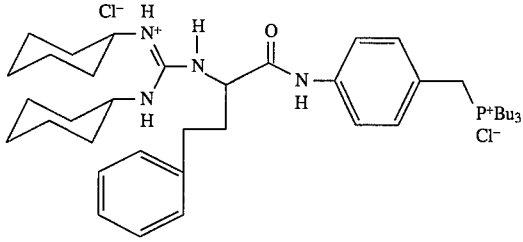 | 4.65 |
| 15 | 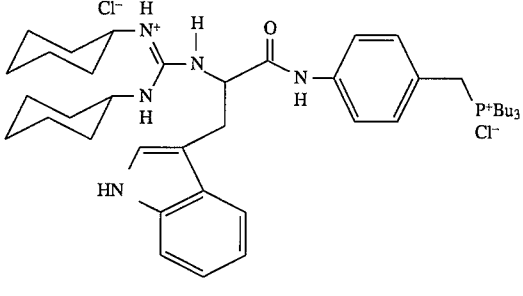 | 2.70 |
| 16 | 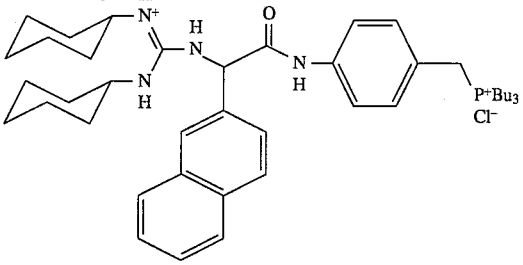 | 3.44 |

TABLE I-continued

| Comp. of Example | Structure | IMR 90 Ki (μM) |
|---|---|---|
| 17 | (structure with dicyclohexyl guanidinium, naphthylmethyl, amide to benzyl-P⁺Bu₃ Cl⁻) | 3.00 |
| 18 | (structure with dicyclohexyl guanidinium, naphthylmethyl, amide to quinuclidinium HCl) | 0.410<br>0.860<br>0.265<br>0.550 |
| 19 | (structure with dicyclohexyl guanidinium, naphthylmethyl, amide to 4-hydroxymethylphenyl) | 4.95 |
| 20 | (structure with dicyclohexyl guanidinium, naphthylmethyl, amide to quinolinyl) | 1.30 |
| 21 | (structure with dicyclohexyl guanidinium, naphthylmethyl, amide to pyridinyl) | 3.15 |
| 22 | (structure with dicyclohexyl guanidinium, 4-chlorobenzyl, amide to quinuclidinium HCl) | 2.90 |

TABLE I-continued

| Comp. of Example | Structure | IMR 90 Ki (μM) |
|---|---|---|
| 23 | 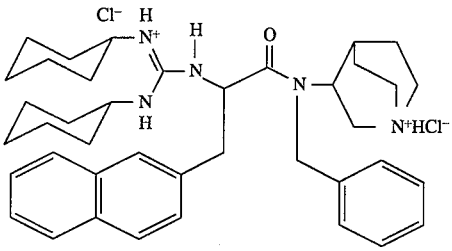 | 0.830 |
| 24 | 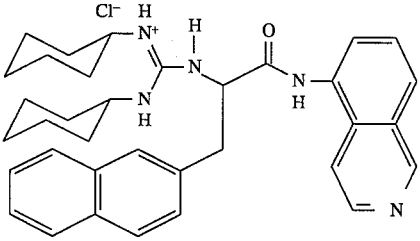 | 2.54 |
| 25 | 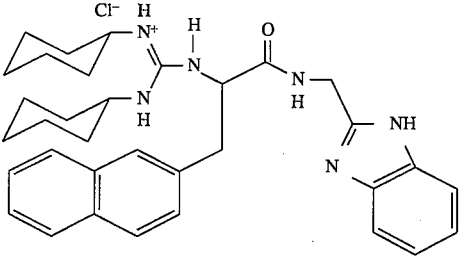 | 5.30 |
| 26 | 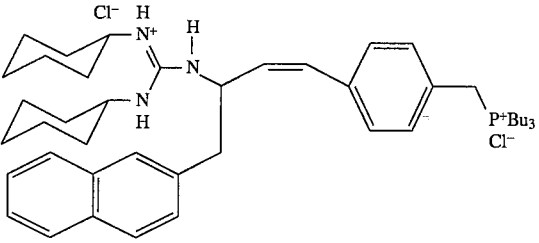 | 0.760 |
| 27 | 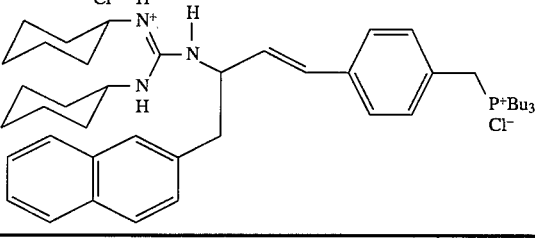 | 0.250 |

The novel nonpeptide compounds having bradykinin antagonist activity may be used for the treatment of traumatic, inflammatory or pathological conditions which are known to be mediated by bradykinin.

These conditions include local trauma such as wounds, burns and rashes, angina, arthritis, asthma, allergies, rhinitis, shock, inflammatory bowel disease, low blood pressure, systemic treatment of pain and inflammation, ischemia secondary to head trauma, oncological diseases and low sperm motility which produces male infertility. The bradykinin antagonists may be advantageously administered in a variety of ways including sublingual absorption, or patch administration using agents for assisting absorption through the skin such as for the treatment of angina; subcutaneously, intravenously or in the form of sprays or rectally in the form of suppositories, or orally in the form of solids in a pharmaceutically acceptable carrier.

Suitable carriers are known in the art and include solids, liquids or mixtures thereof. Solid forms include powders, tablets and capsules which may contain flavoring agents, lubricants, suspending agents and the like. The solid forms preferably contain from about 5 to about 95% of the active nonpeptide. Suitable solid carriers include magnesium carbonate, magnesium stearate, talc, sugars, starch, gelatin, sodium carboxymethyl cellulose and the like.

Liquid forms of the compositions include sterile solutions, suspensions, emulsions, syrups and elixirs. The nonpeptide compounds are dissolved in aqueous or organic solvents or a mixture thereof.

Preferably the pharmaceutical composition of the present invention is in unit dosage form. The quantity of the active ingredient in a unit dosage form may be varied from about 5 to about 500 mg or more according to the particular need. The physician will determine the dosage based on the pathological condition, age and other characteristics of the patient.

The invention, having been fully described, it will be apparent to one skilled in the art that changes and modifications can be made thereto without departing from the spirit and scope thereof.

$R^6$ is

[structure: vinyl-phenyl-$P^+(alkyl)_3$]

and
$R^7$ is H or alkyl.

2. The nonpeptide bradykinin antagonist compound of claim 1 selected from the group consisting of: Phosphonium, [[4-[[2-[[bis(cyclohexylamino)methylene]amino]-3-(2-naphthalenyl)-1-oxopropyl]amino]phenyl]methyl]tributyl-, chloride,monohydrochloride; Phosphonium[[4-[[2-[[bis(cyclohexyl-amino)methylene]amino]-1-oxo-3-phenylpropyl] amino]phenyl]methyl]tributylchloride, monohydrochloride; Phosphonium, [[4-[[3-(4-benzoylphenyl)-2-[[bis(cyclohexylamino)methylene]amino]-1-oxopropyl]amino]phenyl]

---

---

What is claimed is:

1. A nonpeptide bradykinin receptor antagonist compound of the formulae (I) and (II)

[structure (I)]

[structure (II)]

or a pharmaceutically acceptable salt thereof
wherein
$R^1$ and $R^2$ are independently H, phenyl-substituted or unsubstituted alkyl, cycloalkyl or phenyl in which one or two hydrogen atoms are optionally replaced by lower-alkyl;
$R^3$ is phenyl, halophenyl, naphthyl or phenyl—C(=)-phenylene;
$R^4$ is phenyl substituted with -alkyl-$P^+(alkyl)_3$;
$R^5$ is H or alkyl;

methyl]tributyl-, chloride, monohydrochloride; Phosphonium, [[4-[[2-bis(2-methylethylamino)methylene]amino]-3-(2-naphthalenyl)-1-oxopropyl]amino]phenyl]methyl] tributyl-, chloride, monohydrochloride; and Phosphonium, [[4-[[2-[[bis(cyclohexylamino)methylene]amino]-3-(2-naphthalenyl)-1-oxopropyl]amino]phenyl]methyl]tributyl-, chloride,monohydrochloride.

3. The nonpeptide bradykinin antagonist compound of claim 1 selected from the group consisting of: Phosphonium, [[4-[[2-[[bis(cyclohexylamino)methylene]amino]-3-(2-naphthalenyl)-1-oxopropyl]amino]phenyl]methyl]tripentyl-, chloride,monohydrochloride; Phosphonium, [[4-[[2-[[bis(cyclohexylamino)methyleneamino]-3-(2 -naphthalenyl)-1-oxopropyl]amino]phenyl]methyl]triphenyl-, chloride,monohydrochloride; Phosphonium, [[4-[[2- [[bis(cyclohexylamino)methylene]amino]-3-(1-naphthalenyl)-1-oxopropyl]amino]phenyl]methyl]tributyl-, chloride, monohydrochloride; and Phosphonium, tributyl[[4-[[3-(2-naphthalenyl)-1-oxo-2-[[[(3-phenylpropyl)amino] (propylamino)methylene]amino]propyl]amino]phenyl] methyl]-, chloride, monohydrochloride.

4. The nonpeptide bradykinin antagonist compound of claim 1 selected from the group consisting of: Phosphonium, [[4-[[2-[[bis(cyclohexylamino)methylene]N-methylamino]-3-(2-naphthalenyl)-1-oxopropyl]amino]phenyl]methyl] tributyl-, chloride, monohydrochloride; Phosphonium, [[4-[[2-[[bis[(4-methylphenyl)amino]methylene]amino]-3-(2-naphthalenyl)-1-oxopropyl]amino]phenyl]methyl]tributyl-, chloride, monohydrochloride; and Phosphonium, [[4-[[2-[[bis(cyclohexylamino)methylene]amino]-1-oxo-4-phenylbutyl]amino]phenyl]methyl]tributyl-, chloride, monohydrochloride.

5. The nonpeptide bradykinin antagonist compound of claim 1 selected from the group consisting of: Phosphonium, [[4-[[[[bis(cyclohexylamino)methylene]amino]-2-naphthalenylacetyl]amino]phenyl]methyl] tributyl-, chloride, monohydrochloride; and Phosphonium, [[3-[[2-bis(cyclohexylamino)methylene]amino]-3-(2-naphthalenyl)-1-oxopropyl]amino]phenyl]methyl]tributyl-, chloride, monohydrochloride.

6. A pharmaceutical composition comprising a nonpeptide bradykinin antagonist of the formulae (I) and (II)

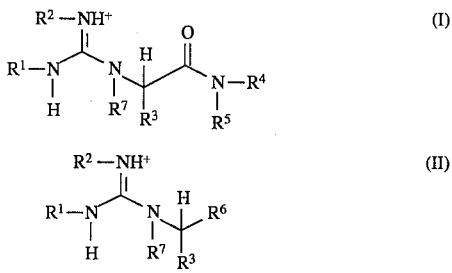

or a pharmaceutically acceptable salt thereof wherein
$R^1$ and $R^2$ are independently H, phenyl-substituted or unsubstituted alkyl, cycloalkyl or phenyl in which one or two hydrogen atoms are optionally replaced by lower-alkyl;
$R^3$ is phenyl, halophenyl, naphthyl or phenyl—C(=O)-phenylene;
$R^4$ is phenyl substituted with -alkyl-$P^+$(alkyl)$_3$;
$R^5$ is H or alkyl;
$R^6$ is

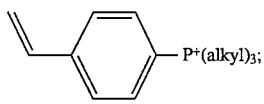

and
$R^7$ is H or alkyl in combination with a pharmaceutically acceptable carrier.

7. The pharmaceutical composition of claim 6 comprising a compound selected from the group consisting of: Phosphonium, [[4-[[2-[[bis(cyclohexylamino)methylene]amino]-3-(2-naphthalenyl)-1-oxopropyl]amino]phenyl]methyl]tributyl-, chloride,monohydrochloride; Phosphonium[[4-[2-[[bis(cyclohexyl-amino)methylene]amino]-1-oxo-3-phenylpropyl]amino]phenyl]methyl]tributylchloride, monohydrochloride; Phosphonium, [[4-[[3-(4-benzoylphenyl)-2-[[bis(cyclohexylamino)methylene]amino]-1-oxopropyl]amino]phenyl]methyl]tributyl-, chloride, monohydrochloride; Phosphonium, [[4-[[2-[bis(2-methylethylamino)methylene]amino]-3-(2-naphthalenyl)-1-oxopropyl]amino]phenyl]methyl]tributyl-, chloride, monohydrochloride; and Phosphonium, [[4-[[2-[[bis(cyclohexylamino)methylene]amino]-3-(2 -naphthalenyl)-1-oxopropyl]amino]phenyl]methyl]tributyl-, chloride,monohydrochloride.

8. The pharmaceutical composition of claim 6 comprising a compound selected from the group consisting of: Phosphonium, [[4-[[2-[[bis(cyclohexylamino)methylene]amino]-3-(2-naphthalenyl)-1-oxopropyl]amino]phenyl]methyl]tripentyl-, chloride, monohydrochloride; Phosphonium, [[4-[[2-[[bis(cyclohexylamino)methyleneamino]-3-(2-naphthalenyl)-1-oxopropyl]amino]phenyl]methyl]triphenyl-, chloride,monohydrochloride; Phosphonium, [[4-[[2-[[bis(cyclohexylamino)methylene]amino]-3-(1-naphthalenyl)-1-oxopropyl]amino]phenyl]methyl]tributyl-, chloride, monohydrochloride; and Phosphonium, tributyl[[4-[[3-(2-naphthalenyl)-1-oxo-2-[[[(3-phenylpropyl)amino](propylamino)methylene]amino]propyl]amino]phenyl]methyl]-, chloride, monohydrochloride.

9. The pharmaceutical composition of claim 6 comprising a compound selected from the group consisting of:

Phosphonium, [[4-[[2-[[bis(cyclohexylamino)methylene]N-methylamino]-3-(2-naphthalenyl)-1-oxopropyl]amino]phenyl]methyl]tributyl-, chloride, monohydrochloride; Phosphonium, [[4-[[2-[[bis[(4-methylphenyl)amino]methylene]amino]-3-(2-naphthalenyl)-1-oxopropyl]amino]phenyl]methyl]tributyl-, chloride, monohydrochloride; and Phosphonium, [[4-[[2-[[bis(cyclohexylamino)methylene]amino]-1-oxo-4-phenylbutyl]amino]phenyl]methyl]tributyl-, chloride, monohydrochloride.

10. The pharmaceutical composition of claim 6 comprising a compound selected from the group consisting of:

Phosphonium, [[4-[[[[bis(cyclohexylamino)methylene]amino]-2-naphthalenylacetyl]amino]phenyl]methyl]tributyl-, chloride, monohydrochloride; and Phosphonium, [[3-[[2-[[bis(cyclohexylamino)methylene]amino]-3-(2 -naphthalenyl)-1-oxopropyl]amino]phenyl]methyl]tributyl-, chloride, monohydrochloride.

11. A method for the inhibition of bradykinin in a mammal comprising: administering to said mammal an effective bradykinin inhibiting amount of the pharmaceutical composition of claim 6.

12. The method of claim 11 wherein said inhibition of bradykinin is to treat inflammatory conditions in a mammal.

* * * * *

SEQUENCE LISTING ( 1 ) GENERAL INFORMATION:

( i i i ) NUMBER OF SEQUENCES:1

( 2 ) INFORMATION FOR SEQ ID NO:1:

( i ) SEQUENCE CHARACTERISTICS:
        ( A ) LENGTH:8 Amino Acid Residues
        ( B ) TYPE:Amino Acid
        ( C ) STRANDEDNESS:
        ( D ) TOPOLOGY:Linear ( i i ) MOLECULE TYPE:Peptide
        ( A ) DESCRIPTION:

( i x ) SEQUENCE DESCRIPTION: SEQ ID NO:1:

Arg  Pro  Pro  Gly  Phe  Pro  Phe  Arg
                             5